(12) United States Patent
Ouyang et al.

(10) Patent No.: US 11,350,816 B2
(45) Date of Patent: Jun. 7, 2022

(54) PORTABLE AND ERGONOMIC ENDOSCOPE WITH DISPOSABLE CANNULA

(71) Applicant: MicronVision Corp., Bellevue, WA (US)

(72) Inventors: Xiaolong Ouyang, Bellevue, WA (US); Shih-Ping Wang, Los Altos, CA (US)

(73) Assignee: Micron Vision Corp., Bellevue, WA (US)

( * ) Notice: Subject to any disclaimer, the term of this patent is extended or adjusted under 35 U.S.C. 154(b) by 0 days.

(21) Appl. No.: 17/362,043

(22) Filed: Jun. 29, 2021

(65) Prior Publication Data

US 2022/0079418 A1  Mar. 17, 2022

Related U.S. Application Data

(60) Provisional application No. 63/183,151, filed on May 3, 2021, provisional application No. 63/153,252, filed on Feb. 24, 2021, provisional application No. 63/149,338, filed on Feb. 14, 2021, provisional application No. 63/138,751, filed on Jan. 18, 2021, provisional application No. 63/129,703, filed on Dec.
(Continued)

(51) Int. Cl.
*A61B 1/00* (2006.01)
*A61B 1/005* (2006.01)

(52) U.S. Cl.
CPC .......... *A61B 1/0052* (2013.01); *A61B 1/0016* (2013.01); *A61B 1/00039* (2013.01); *A61B 1/0057* (2013.01); *A61B 1/00103* (2013.01); *A61B 1/00119* (2013.01)

(58) Field of Classification Search
CPC ............ A61B 1/00052; A61B 1/00119; A61B 1/00105; A61B 1/0057; A61B 1/0016; A61B 1/00039; A61B 1/00103
See application file for complete search history.

(56) References Cited

U.S. PATENT DOCUMENTS

| | | |
|---|---|---|
| 5,667,472 A | 9/1997 | Finn et al. |
| 6,211,904 B1 | 4/2001 | Adair et al. |

(Continued)

FOREIGN PATENT DOCUMENTS

WO   2016137838   9/2016

OTHER PUBLICATIONS

International Search Report and Written Opinion for PCT/US21/50095, dated Dec. 17, 2021.

*Primary Examiner* — Alexandra L Newton
*Assistant Examiner* — Rynae Boler
(74) *Attorney, Agent, or Firm* — Wissing Miller LLP

(57) ABSTRACT

An endoscopic system includes a single-use portion and a multiple-use portion. The two portions can be mated and un-mated. The single-use portion includes an elongated cannula that has a bendable section near its distal end providing a "steerable" distal tip. The distal tip includes LED illumination and an imaging module that feeds live video to a display screen forming which forms part of the multiple-use portion. Ergonomically designed steering control and significant portions of the steering structure reside in the multiple-use portion. The cannula is configured to rotate, which further expands the field of view when combined with steering deflection along a single axis. Some embodiments, include motorized distal tip deflection and/or omni-directional tip deflection.

22 Claims, 21 Drawing Sheets

Related U.S. Application Data 23, 2020, provisional application No. 63/124,803, filed on Dec. 13, 2020, provisional application No. 63/121,924, filed on Dec. 6, 2020, provisional application No. 63/121,246, filed on Dec. 4, 2020, provisional application No. 63/107,344, filed on Oct. 29, 2020, provisional application No. 63/087,935, filed on Oct. 6, 2020, provisional application No. 63/083,932, filed on Sep. 27, 2020, provisional application No. 63/077,675, filed on Sep. 13, 2020, provisional application No. 63/077,635, filed on Sep. 13, 2020.

(56) References Cited

U.S. PATENT DOCUMENTS

| | | |
|---|---|---|
| 8,361,775 B2 | 1/2013 | Flower |
| 8,952,312 B2 | 2/2015 | Blanquart et al. |
| 2005/0264687 A1 | 1/2005 | Murayama |
| 2006/0259124 A1 | 11/2006 | Matsuoka et al. |
| 2010/0121142 A1 | 5/2010 | OuYang et al. |
| 2010/0157039 A1 | 6/2010 | Sugai |
| 2011/0009694 A1 | 1/2011 | Schultz et al. |
| 2011/0112622 A1 | 5/2011 | Phan et al. |
| 2012/0165916 A1 | 6/2012 | Jordan |
| 2012/0253116 A1* | 10/2012 | Sniffin ............ A61B 1/00066 600/106 |
| 2014/0296866 A1 | 10/2014 | Salman et al. |
| 2015/0011830 A1* | 1/2015 | Hunter ............ A61B 1/0052 600/118 |
| 2015/0018622 A1 | 1/2015 | Tesar et al. |
| 2015/0018710 A1 | 1/2015 | Furlong et al. |
| 2015/0088001 A1 | 3/2015 | Lindvold et al. |
| 2015/0297311 A1 | 10/2015 | Tesar |
| 2016/0367119 A1 | 12/2016 | Ouyang et al. |
| 2018/0132700 A1* | 5/2018 | Ouyang ............ A61B 1/00135 |
| 2018/0256009 A1 | 9/2018 | Ouyang et al. |
| 2019/0142262 A1* | 5/2019 | Inglis ............ A61B 1/00066 600/188 |
| 2019/0216325 A1 | 7/2019 | Ouyang |
| 2019/0223691 A1 | 7/2019 | Takatsuji |
| 2020/0204776 A1 | 6/2020 | Themelis |
| 2021/0401277 A1 | 12/2021 | OuYang et al. |

\* cited by examiner

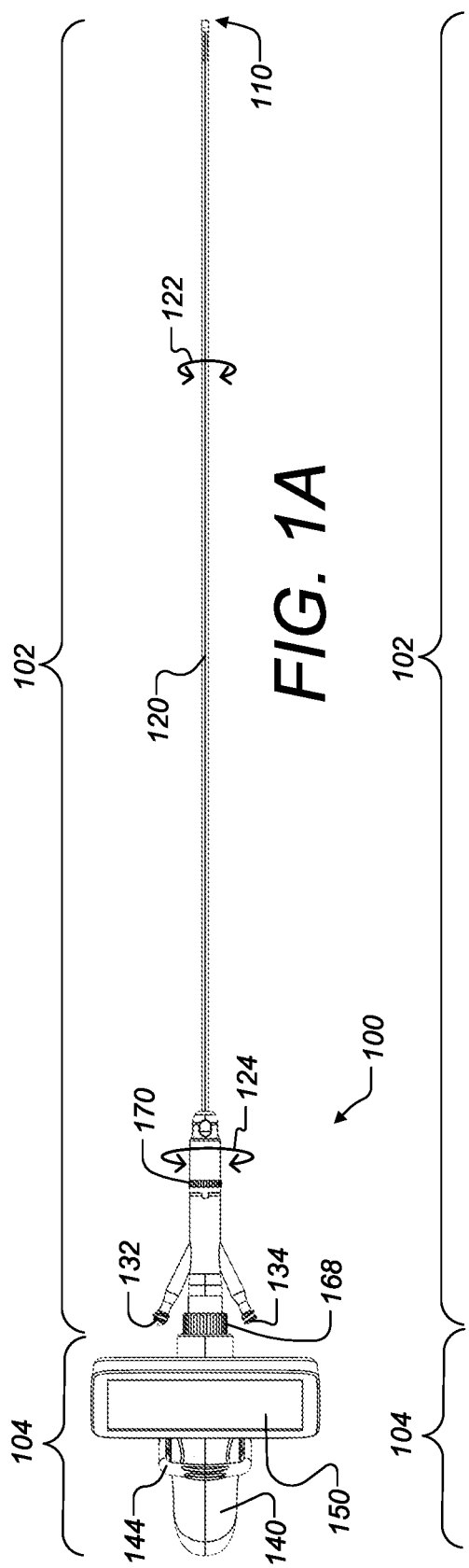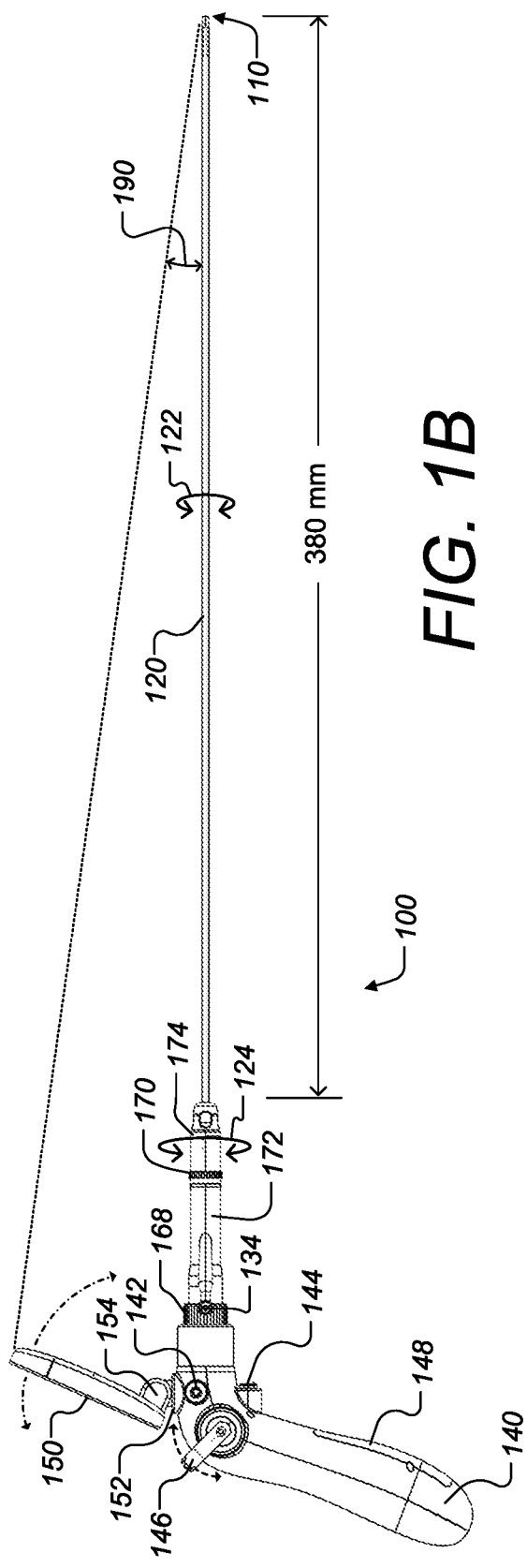

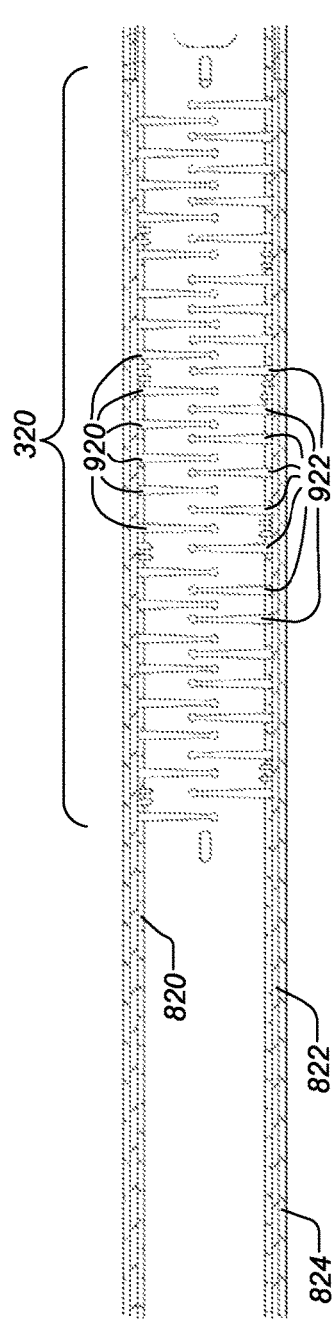
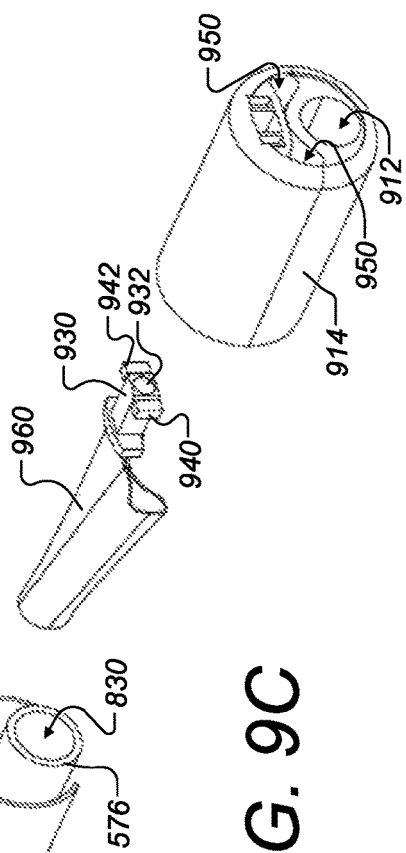
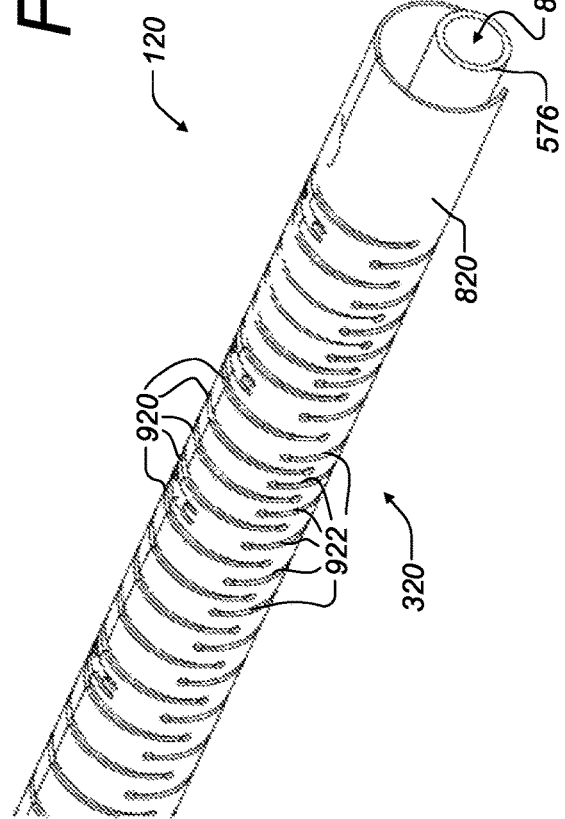

PORTABLE AND ERGONOMIC ENDOSCOPE WITH DISPOSABLE CANNULA

REFERENCE TO RELATED APPLICATIONS

This patent application claims the benefit of and incorporates by reference each of the following provisional applications:
U.S. Prov. Ser. No. 63/183,151 filed May 3, 2021;
U.S. Prov. Ser. No. 63/153,252 filed Feb. 24, 2021;
U.S. Prov. Ser. No. 63/149,338 filed Feb. 14, 2021;
U.S. Prov. Ser. No. 63/138,751 filed Jan. 18, 2021;
U.S. Prov. Ser. No. 63/129,703 filed Dec. 23, 2020;
U.S. Prov. Ser. No. 63/124,803 filed Dec. 13, 2020;
U.S. Prov. Ser. No. 63/121,924 filed Dec. 6, 2020;
U.S. Prov. Ser. No. 63/121,246 filed Dec. 4, 2020;
U.S. Prov. Ser. No. 63/107,344 filed Oct. 29, 2020;
U.S. Prov. Ser. No. 63/087,935 filed Oct. 6, 2020;
U.S. Prov. Ser. No. 63/083,932 filed Sep. 27, 2020;
U.S. Prov. Ser. No. 63/077,675 filed Sep. 13, 2020; and
U.S. Prov. Ser. No. 63/077,635 filed Sep. 13, 2020.

This patent application is also related to and incorporates by reference each of the following international, non-provisional and provisional applications:
International Patent Application No. PCT/US17/53171 filed Sep. 25, 2017;
U.S. Pat. No. 8,702,594 Issued Apr. 22, 2014;
U.S. patent application Ser. No. 16/363,209 filed Mar. 25, 2019;
International Patent Application No. PCT/US19/36060 filed Jun. 7, 2019;
U.S. patent application Ser. No. 16/972,989 filed Dec. 7, 2020;
U.S. Prov. Ser. No. 62/816,366 filed Mar. 11, 2019;
U.S. Prov. Ser. No. 62/671,445 filed May 15, 2018;
U.S. Prov. Ser. No. 62/654,295 filed Apr. 6, 2018;
U.S. Prov. Ser. No. 62/647,817 filed Mar. 25, 2018;
U.S. Prov. Ser. No. 62/558,818 filed Sep. 14, 2017;
U.S. Prov. Ser. No. 62/550,581 filed Aug. 26, 2017;
U.S. Prov. Ser. No. 62/550,560 filed Aug. 25, 2017;
U.S. Prov. Ser. No. 62/550,188 filed Aug. 25, 2017;
U.S. Prov. Ser. No. 62/502,670 filed May 6, 2017;
U.S. Prov. Ser. No. 62/485,641 filed Apr. 14, 2017;
U.S. Prov. Ser. No. 62/485,454 filed Apr. 14, 2017;
U.S. Prov. Ser. No. 62/429,368 filed Dec. 2, 2016;
U.S. Prov. Ser. No. 62/428,018 filed Nov. 30, 2016;
U.S. Prov. Ser. No. 62/424,381 filed Nov. 18, 2016;
U.S. Prov. Ser. No. 62/423,213 filed Nov. 17, 2016;
U.S. Prov. Ser. No. 62/405,915 filed Oct. 8, 2016;
U.S. Prov. Ser. No. 62/399,712 filed Sep. 26, 2016;
U.S. Prov. Ser. No. 62/399,436 filed Sep. 25, 2016;
U.S. Prov. Ser. No. 62/399,429 filed Sep. 25, 2016;
U.S. Prov. Ser. No. 62/287,901 filed Jan. 28, 2016;
U.S. Prov. Ser. No. 62/279,784 filed Jan. 17, 2016;
U.S. Prov. Ser. No. 62/275,241 filed Jan. 6, 2016;
U.S. Prov. Ser. No. 62/275,222 filed Jan. 5, 2016;
U.S. Prov. Ser. No. 62/259,991 filed Nov. 25, 2015;
U.S. Prov. Ser. No. 62/254,718 filed Nov. 13, 2015;
U.S. Prov. Ser. No. 62/139,754 filed Mar. 29, 2015;
U.S. Prov. Ser. No. 62/120,316 filed Feb. 24, 2015; and
U.S. Prov. Ser. No. 62/119,521 filed Feb. 23, 2015.

All of the above-referenced non-provisional, provisional and international patent applications are collectively referenced herein as "the commonly assigned incorporated applications."

FIELD

This patent specification generally relates mainly to endoscopes. More particularly, some embodiments relate to portable endoscope devices that include a re-usable handle portion and a disposable or single-use cannula portion.

BACKGROUND

In the case of both rigid and flexible conventional endoscopes, the lens or fiber optic system is relatively expensive and is intended to be re-used many times. Therefore, stringent decontamination and disinfection procedures need to be carried out after each use. Disposable endoscopy is an emerging category of endoscopic instruments. In some cases, endoscopes can be made at a low enough cost for single-use applications. Disposable or single-use endoscopy lessens the risk of cross-contamination and hospital acquired diseases.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

Endoscopes having a deflectable or "steerable" distal tip can be useful in many applications including where more than a fixed field of view would be beneficial. In such cases, a section of the cannula near the distal tip can be configured to be bendable, and controlled by the operator. Examples of such known techniques are discussed in U.S. Pat. Nos. 10,918,268, and 11,013,396, both of which are incorporated by reference herein.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

SUMMARY

According to some embodiments, an endoscope comprises: (a) a multiple-use portion comprising a handle and a bend-control lever extending proximally and/or upwardly therefrom, wherein said handle is shaped and dimensioned for a user's hand to hold said handle while ergonomically reaching and manually thumb-operating said bend-control lever and said handle comprises a force-generating cable driver; and (b) a single-use portion releasably attached to said multiple-use portion and comprising: a fluid hub extending distally from said handle and bend-control lever and having one or more proximal fluid ports; a cannula attached to said fluid hub and extending distally therefrom along a longitudinal axis, wherein said cannula has a bendable distal portion and a distal imaging and further has one or more distal fluid ports; one or more lumens extending from said one or more proximal fluid ports to said one or more distal fluid ports; and steering cables extending from the fluid hub to said bendable portion of the cannula and releasably coupled operatively to said force-generating cable driver in the multiple-use portion. Said bendable portion is coupled with said bend-control lever through said force-generating cable driver such that manual operation of the bend-control lever selectively causes the bendable portion of the cannula to bend to a selected degree in a selected angular direction; and the force-generating cable driver imparts to said cables the force needed to cause said bending.

According to some embodiments, the endoscope can further comprise one or more of the following features: (a) said force-generating cable driver comprises one or more electric motors in said multiple-use portion operatively coupled with said thumb-operated bend-control lever to impart to said steering cables said force needed to cause said bending; (b) said one or more electric motors comprise one or more stepper motors; (c) said force-generating cable driver comprises one or more driving gears driven by said one or more electric motors; (d) said fluid hub comprises one or more driven gears releasably mating with said one or more driving gears and operatively coupled with said steering cables to selectively bend said bendable portion of the cannula in response to rotation of the one or more driven gears; (e) said force-generating cable driver is configured to stop applying to said steering cables the force needed to cause said bending if said bendable portion of the cannula encounters a selected threshold of resistance to bending applied to said cannula by external forces; (f) said force-generating cable driver comprises one or more gears driven by manually imparted motion of said thumb-operated bend-control lever; (g) said thumb-operated bend-control lever comprises a joystick; (h) said thumb-operated bend-control lever comprise a touch-panel; (i) said multiple-use portion further comprises a display screen mounted on said handle and operatively coupled with said imaging module to display images provided thereby, wherein said display screen includes a touch-sensitive area that selectively displays and serves as said touch-panel and responds to touch to thereby cause said force-generating cable driver to selectively bend said bendable portion of the cannula; (j) at least one of (i) said cannula and (ii) a portion of said fluid hub that includes said proximal ports is mounted for selective rotation relative to said handle about said longitudinal axis; (k) which said cannula is mounted for rotation relative to said proximal portion of the fluid hub about said longitudinal axis; (l) a distal portion of the fluid hub includes a collar fixedly secured to the cannula and manually rotatable to thereby rotate the cannula relative said proximal portion of the fluid hub about said longitudinal axis; (m) said proximal portion of the fluid hub is mounted for rotation relative to the handle about said longitudinal axis; (n) said proximal portion of the fluid hub includes a collar fixedly secured thereto and rotatable by hand to thereby rotate the proximal portion of the fluid hub relative to the handle about said longitudinal axis; (o) said cannula is mounted for rotation relative to said proximal portion of the fluid hub and said proximal portion of the fluid hub is mounted for rotation relative to said handle; and (p) said multiple-use portion is configured to selectively cause bending of the bendable portion of the cannula concurrently with at least one of the cannula and the proximal portion of the fluid hub rotating relative to the handle.

According to some embodiments, an endoscope comprises: a handle shaped and dimensioned to be grasped by a user's hand while the thumb of said hand ergonomically reaches a proximally facing control portion of the handle; a fluid hub and a cannula extending distally therefrom along a longitudinal axis, said cannula having a distal bendable portion and a distal imaging module; one or more driving gears in the handle and one or more driven gears in the fluid hub mating with said one or more driving gears when the fluid hub is releasably attached to the handle; said one or more driven gears being operatively connected to said distal bendable portion of the cannula to bend said bendable distal portion of the cannula through a selected angle and in a selected angular direction upon rotation of the one or more driven gears; wherein at least one of said cannula and said fluid hub is mounted for rotation relative to the handle when the fluid hub is releasably attached to the handle; wherein said control portion of the handle comprises an interface responding to manual operation with the user's thumb to cause the distal bendable portion of the cannula to bend in a selected angular direction over a selected angle by imparting to said one or more driving gears the force needed to cause said bending; and wherein said handle, fluid hub and cannula are configured for concurrent bending of said distal bendable portion of the cannula and rotation of at least of the cannula and the fluid hub relative to the handle.

According to some embodiments, the endoscope described in the immediately preceding paragraph can further comprise one or more of the following features: (a) said handle, fluid hub and cannula are configured for concurrent bending of said bendable portion of the cannula and rotation of each of the cannula and the fluid hub relative to the handle to thereby provide an omnidirectional view of said imaging module; and (b) said bendable portion of the cannula is configured for bending in more than one plane.

According to some embodiments, a method comprises: releasably assembling (a) a multiple-use portion comprising a handle and a display screen mounted thereon with (b) a single use portion comprising (i) a fluid hub with one or more proximal fluid ports and (ii) a cannula extending distally from the fluid hub and having a bendable distal portion, a distal imaging module, and one or more distal ports, wherein said single-use portion further includes one or more lumens connecting said one or more proximal and distal fluid ports; manually operating a bending control mounted on the handle of said multiple-use portion to thereby bend said bendable portion of the cannula through a selected angle in a selected angular direction; selectively rotating at least one of the cannula and the fluid hub relative to the handle while bending said bendable portion of the cannula to thereby omnidirectionally point said imaging module; displaying images from said imaging module on said display screen; and disassembling said multiple-use portion from said single-use portion by hand, without a need for tools, and disposing of the single-use portion after a patient procedure to thereby retain the multiple-use portion for assembling with another single-use portion.

The method can additionally include operating the bending control comprises using the thumb of the hand holding the handle to operate a lever extending proximally from the handle.

As used herein, the grammatical conjunctions "and", "or" and "and/or" are all intended to indicate that one or more of the cases, object or subjects they connect may occur or be present. In this way, as used herein the term "or" in all cases indicates an "inclusive or" meaning rather than an "exclusive or" meaning.

As used herein the terms "surgical" or "surgery" refer to any physical intervention on a patient's tissues, and does not necessarily involve cutting a patient's tissues or closure of a previously sustained wound.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

FIGS. 1A, 1B and 1C are side, top and rear views of a portable and ergonomic endoscope with disposable cannula, according to some embodiments;

FIG. 9B is a partial cross-section view of a cannula used in a portable and ergonomic endoscope, according to some embodiments;

FIG. 9C is a partially exploded perspective view of the distal tip of a portable and ergonomic endoscope, according to some embodiments;

DETAILED DESCRIPTION

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

Figure 1C:
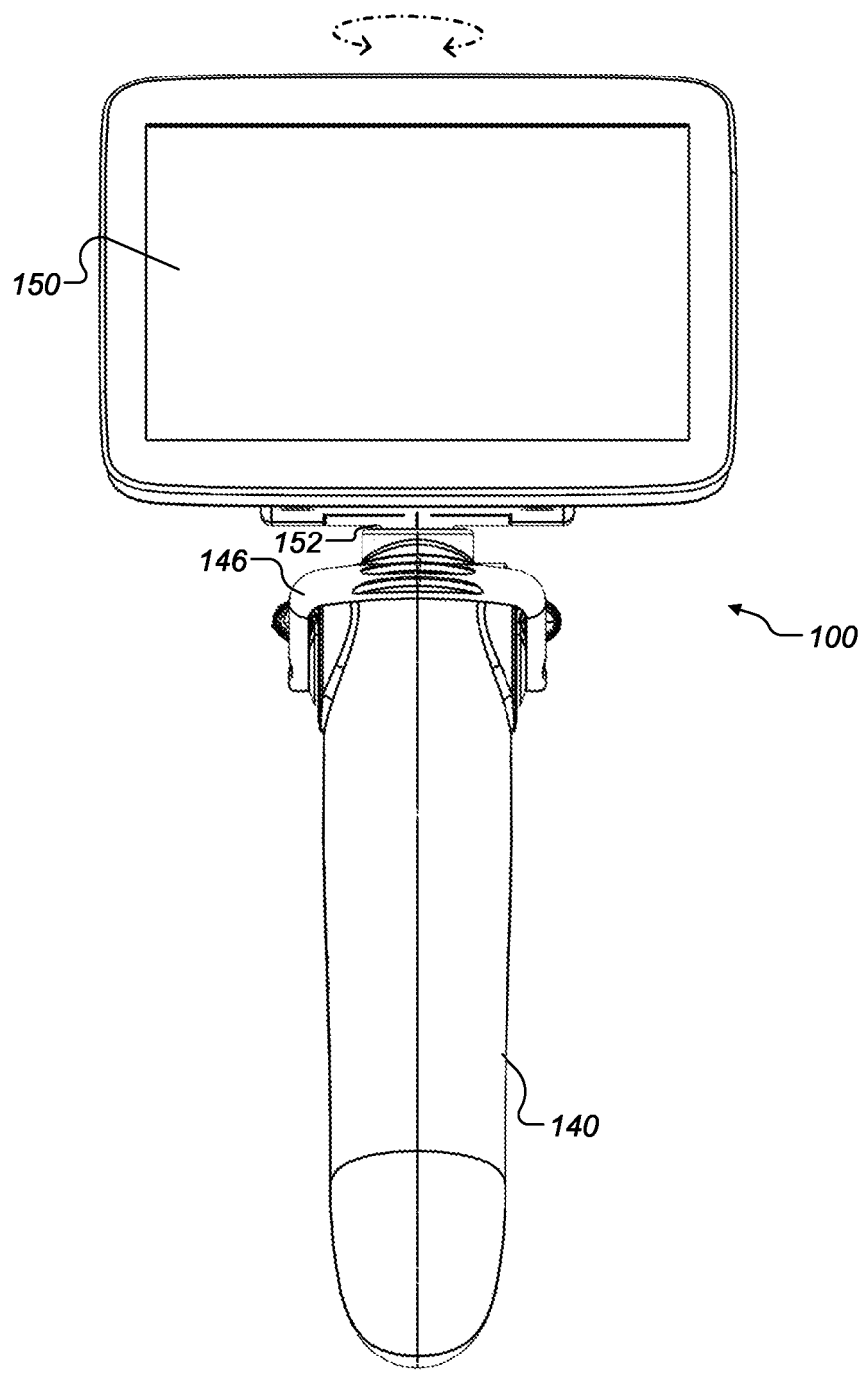

FIGS. 1A, 1B and 1C are side, top and rear views of a portable and ergonomic endoscope with disposable cannula, according to some embodiments. System 100 is adapted for easy and quick use with minimized patient discomfort and high placement accuracy. System 100 is made up of a disposable, or single-use portion 102 and a re-usable portion 104. The two portions 102 and 104 can be mated and un-mated with each other via connectors as will be shown and discussed infra in further detail. Cannula 120 has an imaging and illumination modules on its distal tip 110. An electrical cable (not shown) is positioned within the cannula and supplies control signals and power to the camera and LED illumination modules on distal tip 110 and also transmits video image data from the camera module to the hand piece 140 and display 150 for viewing by an operator. In the example shown, hand piece 140 includes two control buttons 142 and 144 which can be configured for power on/off and image capture, respectively. According to some embodiments, hand piece 140 is shaped as a pistol grip as shown and includes a rechargeable battery (not shown) that is accessible via battery door 148. According to some embodiments, electronics (not shown) within hand piece 140 are configured for video capture, processing and display on display 150. According to some embodiments, display 150 can both tilt and swivel to provide optimal viewing angle for the operator. Swivel joint 152 is configured to provide swiveling of display 150 as shown by the dash dot arrow in FIG. 10, and hinge joint 154 is configured to provide tilting of display 150 as shown by the dash dot arrows in FIG. 1B. According to some embodiments, the hinge joint is configured to allow for tilting of display in the distal direction of about 90 degrees, or nearly 90 degrees. Such tilting can be useful, for example, when give the operator an unobstructed or less obstruct view. Handle 140 also includes a thumb lever 146 that can be moved upwards or downwards as shown by the dashed arrows. Moving the thumb lever 146 upwards and downwards, as will be shown and described in further detail infra, causes the distal tip 110 to bend upwards and downwards, respectively.

The cannula 120 is connected proximally to a fluid hub 172 including in this example two fluid ports 132 and 134. Proximal to the fluid hub is a collar 168. According to some embodiments, the collar 168 is configured to rotate so as to allow for a "plug and twist lock" style mating of portions 102 and 104, as will be shown and described in further detail infra. According to some embodiments, distally from hub 172 is a textured collar 170 and portion 174 that is manually rotatable relative to hub 172 and handle 140 along the main longitudinal axis of cannula 120, as shown by solid arrow 124. Collar 170 and portion 174 are in a fixed rotational relationship with cannula 120 and distal tip 110. Thus, rotating collar 170 and portion 174 causes rotation of cannula 120 and distal tip 110 as shown by solid arrow 124. According to some embodiments, the combination of rotating collar 170 and moving the thumb lever 146, the user can "steer" the direction of distal tip as desired. According to some embodiments, the cannula 120 has a working length in the range of 320 mm to 400 mm, and an outer diameter ranging from 1 mm to 7 mm. According to some embodiments, cannula 120 has a length of 380 mm length and outer diameter of 5.5 mm or less.

Figure 2A:
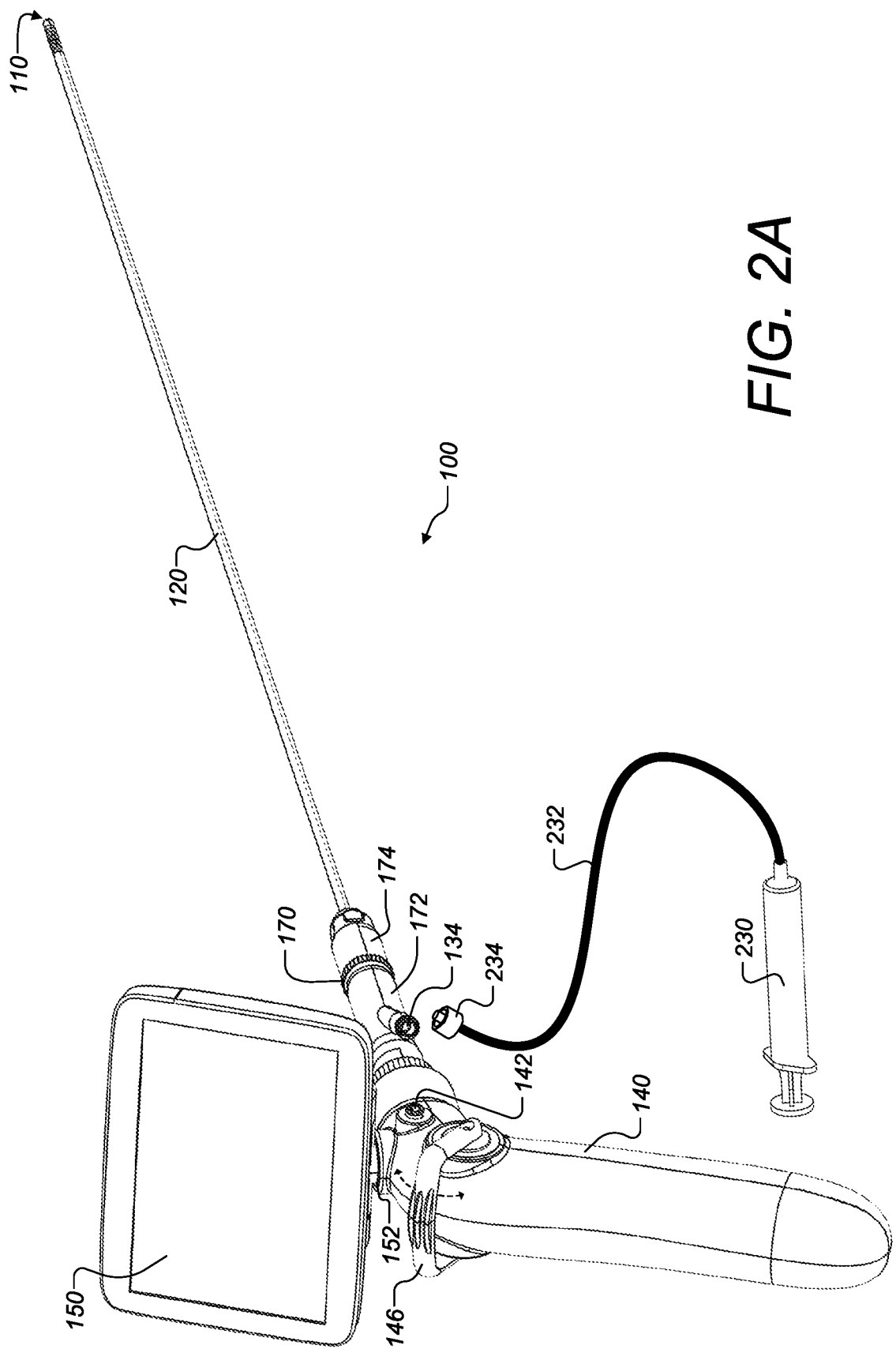
FIGS. 2A and 2B are perspective views of a portable and ergonomic endoscope with disposable cannula, according to some embodiments.
Figure 2B:
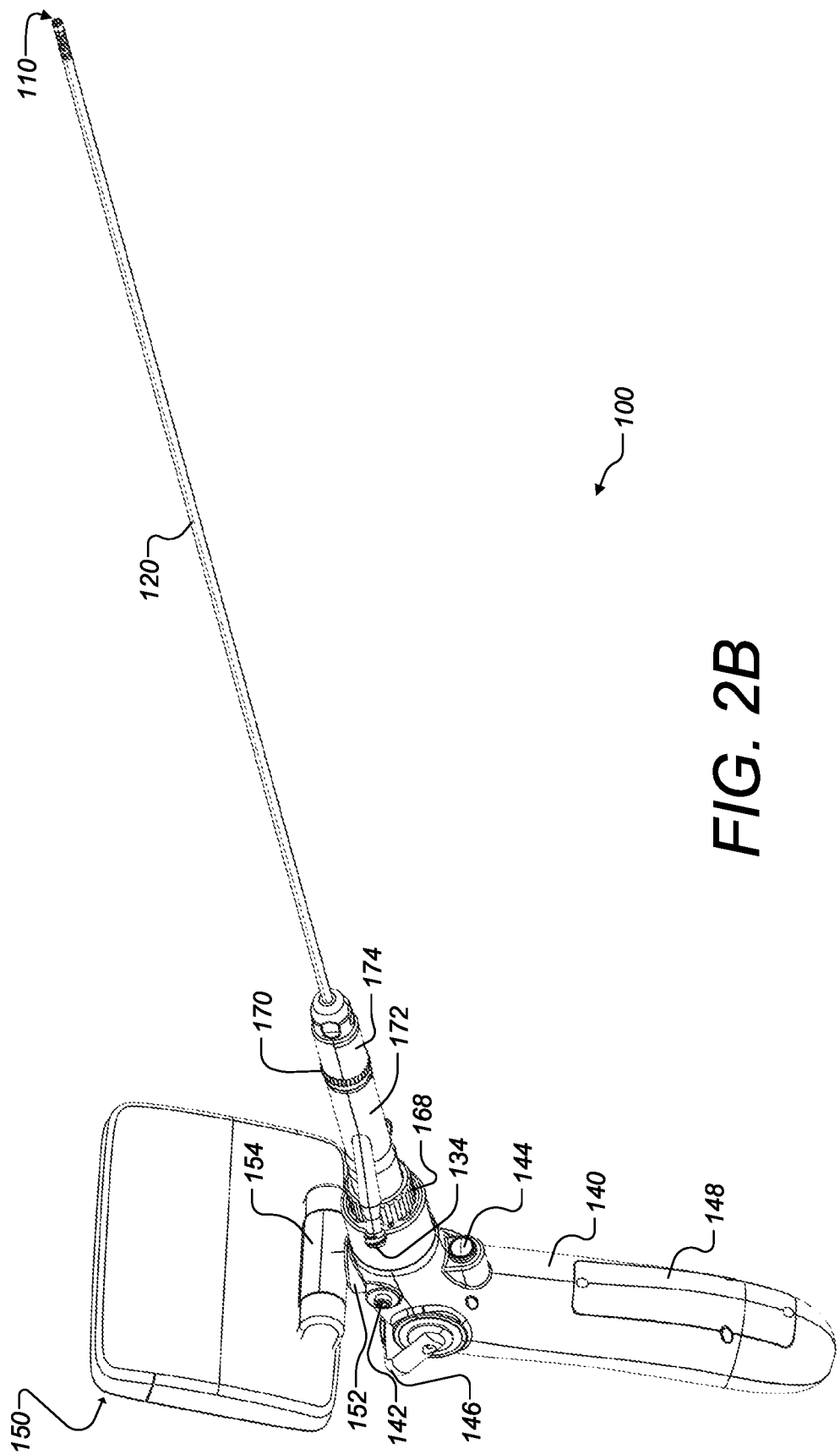

FIGS. 2A and 2B are perspective views of a portable and ergonomic endoscope with disposable cannula, according to some embodiments. FIG. 2A shows a syringe 230 used to supply fluid, such as saline, through a fluid lumen (not shown) within cannula 120 via tubing 232, connector 234 and fluid port 134. According to some embodiments the cannula 120 is semi-rigid. The cannula 120 is stiff enough so it does not collapse with longitudinal pushing and pulling forces. On the other hand, cannula 120 is flexible enough such that it can bend while it passes through curved anatomy.

Figure 3A:
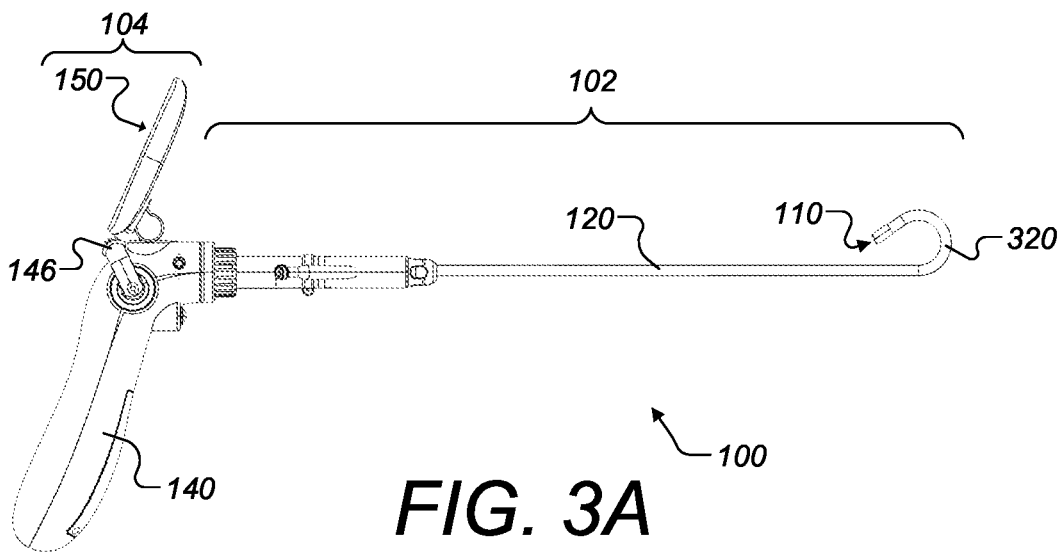
FIGS. 3A-3C are side views of a portable and ergonomic endoscope with disposable cannula configured with a thumb lever for steering of its distal tip, according to some embodiments.
Figure 3B:
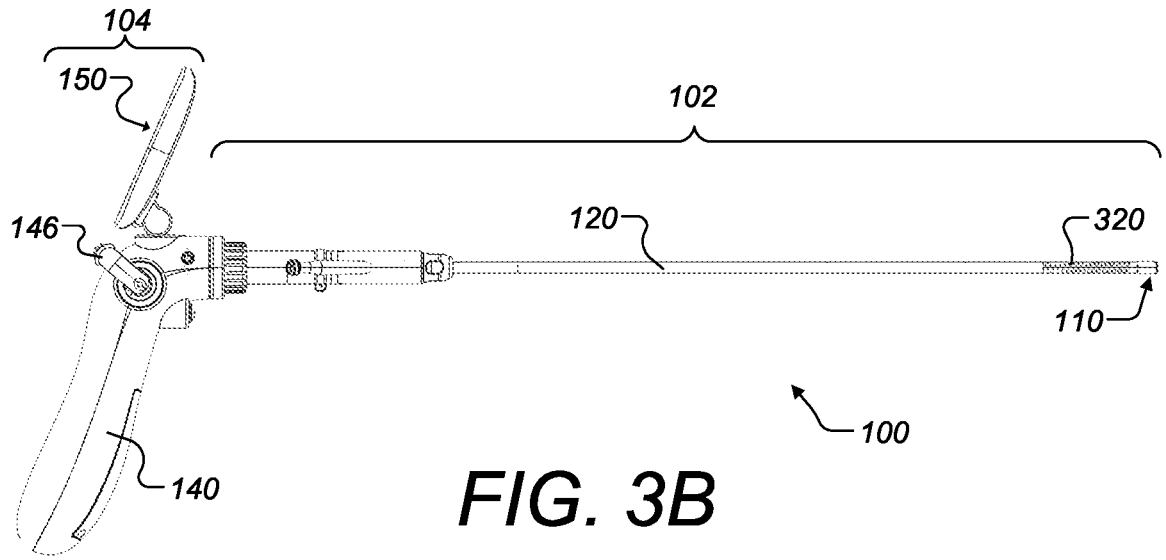
Figure 3C:
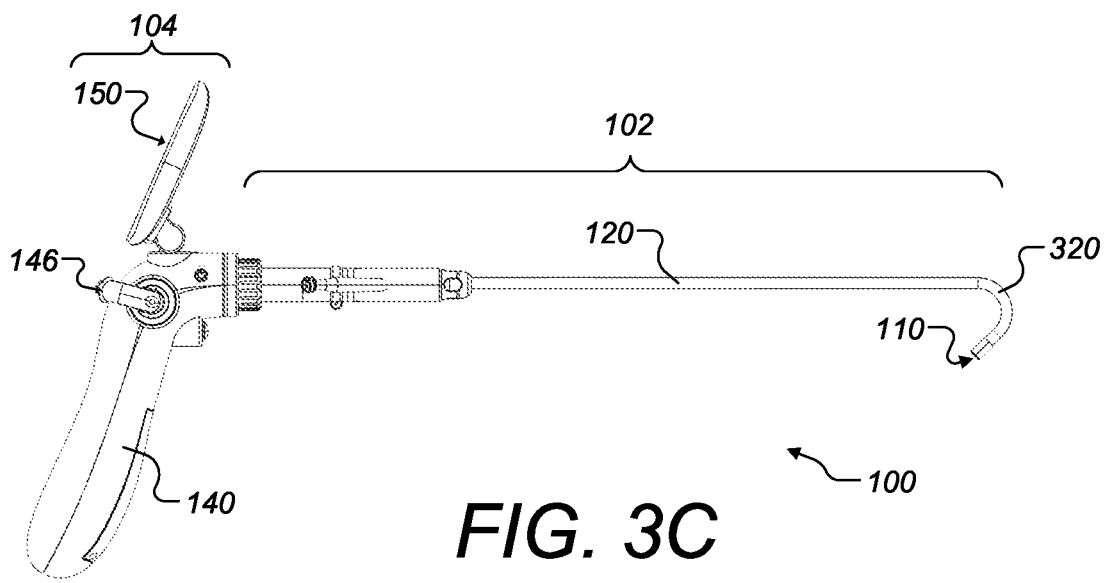

FIGS. 3A-3C are side views of a portable and ergonomic endoscope with disposable cannula configured with a thumb lever for steering of its distal tip, according to some embodiments. FIG. 3A shows system 100 with thumb lever 146 pushed upwards which causes a distal bending section 320 of cannula 120 to bend upwards. FIG. 3B shows system 100 with thumb lever 146 in a middle "neutral position" which causes a distal bending section 320 of cannula 120 to be straight. FIG. 3C shows system 100 with thumb lever 146 pushed downwards which causes a distal bending section 320 of cannula 120 to bend downwards. According to some embodiments, part of the steering structure resides on the reusable hand piece portion 104, to minimize disposable components and increase ergonomics of deflection control. According to some embodiments, the distal bending section 320 has a structural layer, e.g. stainless steel, that includes a plurality of lateral grooves being spaced and arranged to provide suitable upwards and downwards bending characteristics of bending section 320. Further details of possible shape, arrangement and spacing of the grooves in the bending section are discussed in U.S. Pat. No. 10,918,268, which is incorporated herein by reference. According to some embodiments, other structures could be used to implement the bending of the distal tip. For example, known techniques such as "snake bone" arrangements could be used instead of the grooved bending section implementation. According to some embodiments, the amount of bending angulation upwards and downwards is in the range of 130 degrees and 210 degrees. According to some embodiments, the amount of bending is not equal, such as bending upwards of 210 degrees and downwards of 130 degrees. According to some embodiments the system 100 is configured to only bend upwards or only downwards, based on its intended application.

Figure 4A:
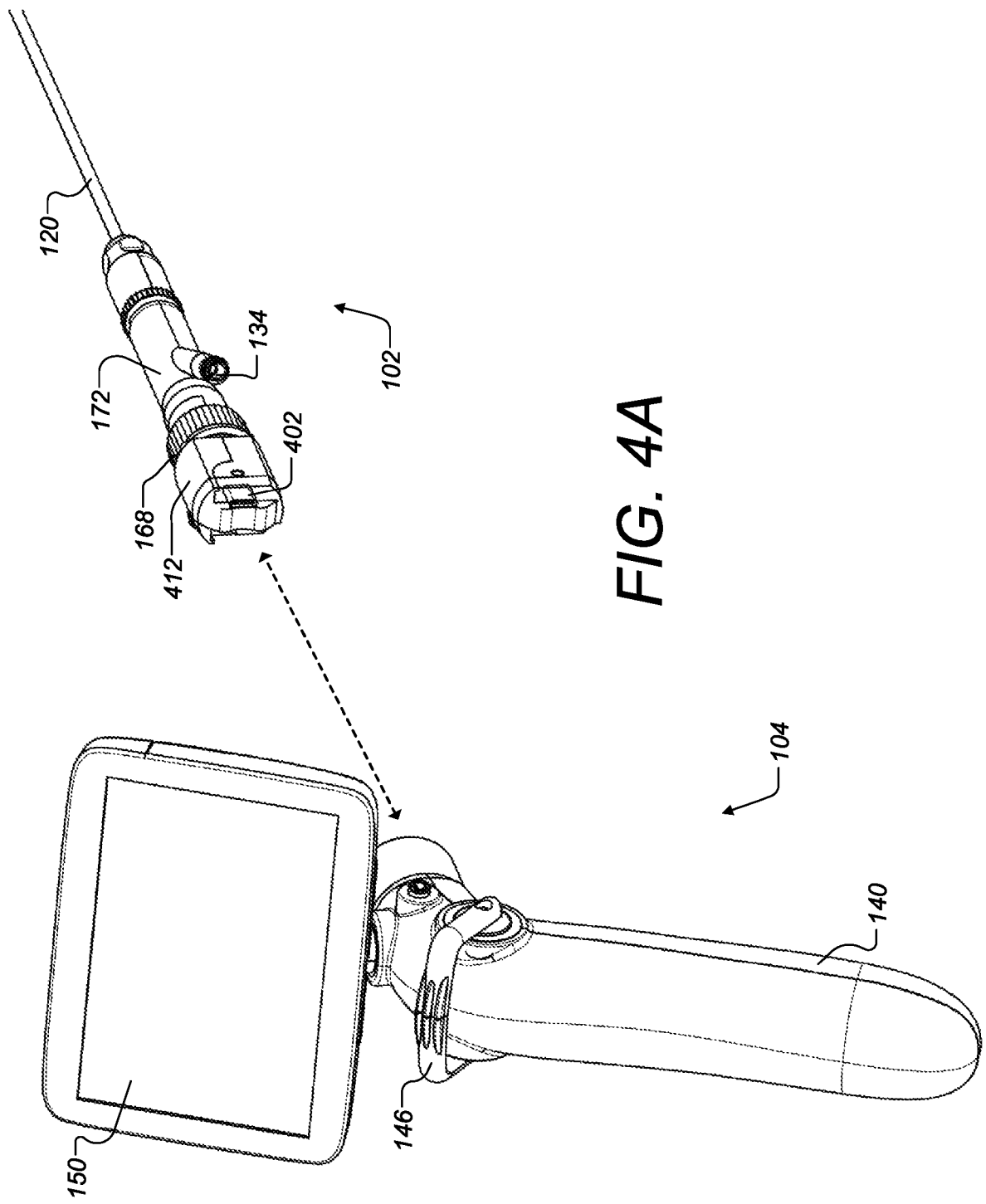
FIGS. 4A-4C are perspective views that illustrate the mating and un-mating of reusable and disposable portions of a portable and ergonomic endoscope, according to some embodiments.
Figure 4B:
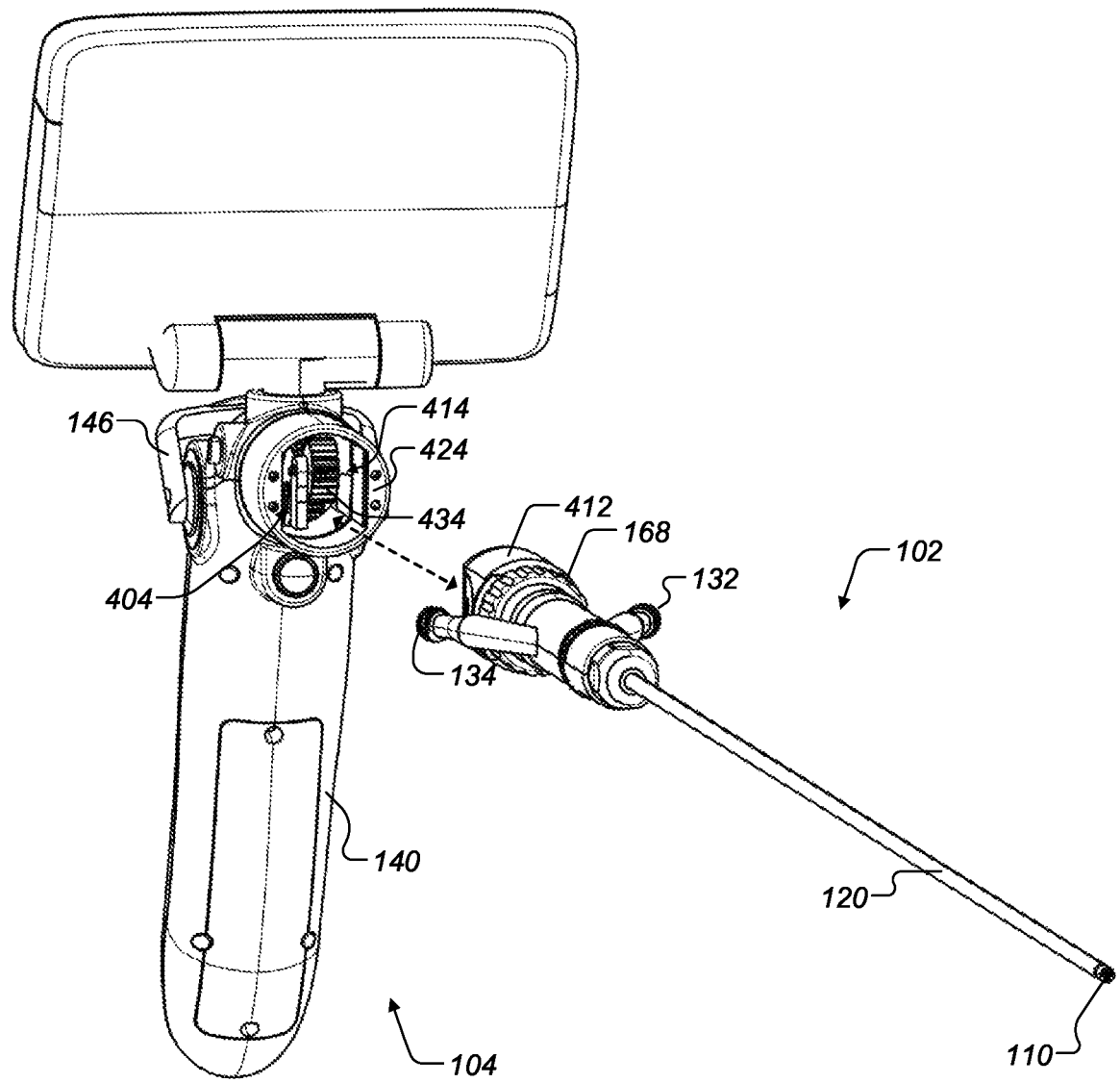
Figure 4C:
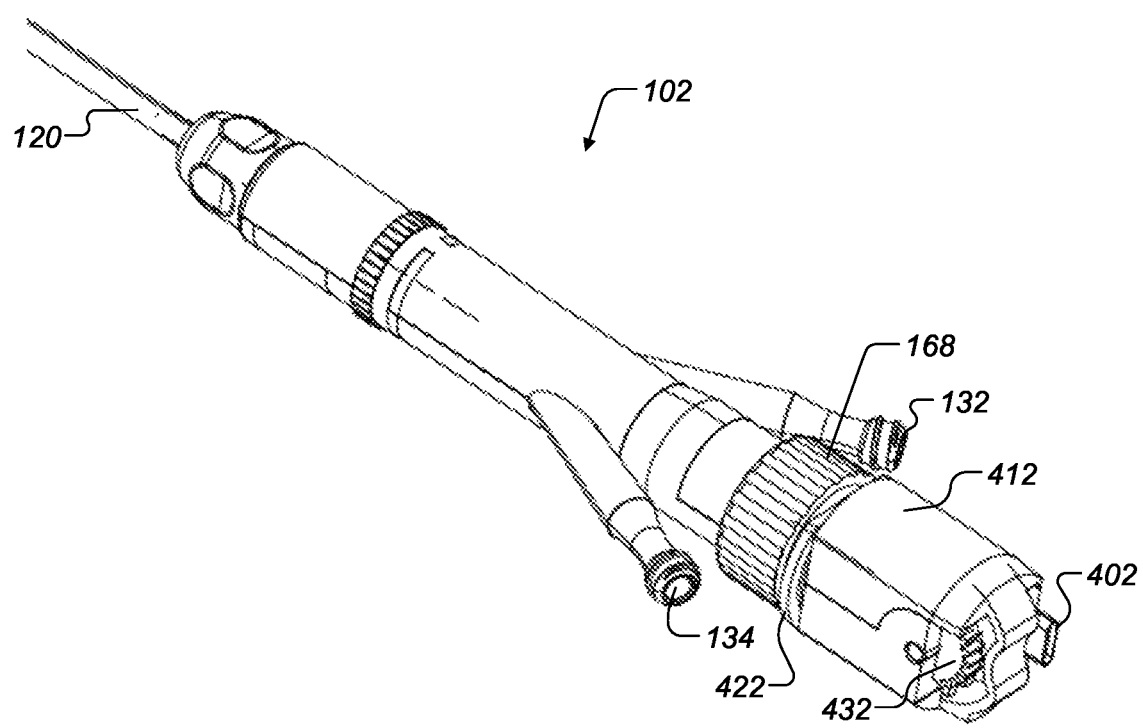

FIGS. 4A to 4C are perspective views that illustrate the mating and un-mating of reusable and disposable portions of a portable and ergonomic endoscope, according to some embodiments. The portions 102 and 104 are connectable and separable via a mechanical and electrical connector. The electrical connection is made via a USB-C type plug 402 on single-use portion 102 (visible in FIGS. 4B and 4C) and USB-C type receptacle 404 on multiple use portion 104 (FIG. 4A). The mechanical connection includes both a structural connection to fixedly attach portions 102 and 104 as well as a steering connection, through which steering input from the steering structure in the re-usable portion 104 can be relayed to the steering components in the single-use portion 102. The structural connection, in this example, includes a male cylindrical portion 412 on single-use portion 102 that is shaped to fit snugly into a female socket 414 on multiple-use portion 104. The structural connection also includes a twist lock type mechanism wherein a male portion 422 can be inserted past a female opening 424 and then locked by twisting the male portion 422 approximately one quarter turn (90 degrees). The twisting action can be applied manually via textured or knurled ring collar 168. In this way, the connection can be configured as a "plug and twist" type connection. The steering connection is provided by meshing the transmission gear 434 on the multiple-use portion 104 with the passive gear 432 on the single-use portion 102.

Figure 5:
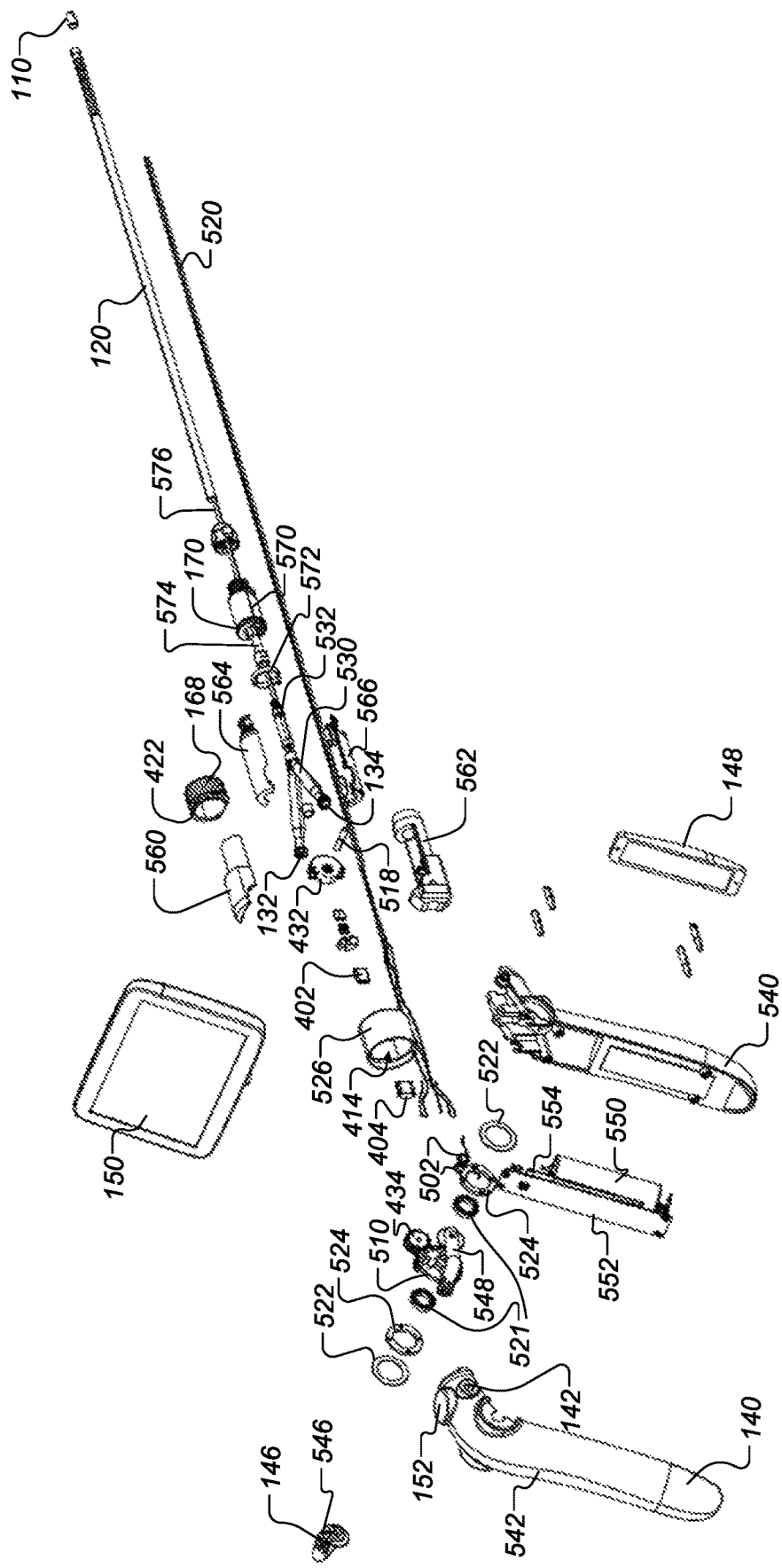
FIG. 5 is an exploded-view diagram of a portable and ergonomic endoscope with disposable cannula, according to some embodiments.

FIG. 5 is an exploded-view diagram of a portable and ergonomic endoscope with disposable cannula, according to some embodiments. Rotatable portion 570 is shown that includes textured collar 170. According to some embodiments, the rotatable portion 570 is formed from two pieces that are bonded together. Collar 572 is configured to hold upper and lower covers 564 and 566 together. The non-rotating portion of the hub body is formed of upper and lower covers 564 and 566, which house the luer fork piece 530. According to some embodiments, both the fluid ports 132 and 134 are connected to a single fluid channel using fork piece 530. Fork piece 530 is attached to channel piece 532. The distal end of channel piece 532 is inserted into the proximal end of outer sleeve 574. One or more o-rings can be used to seal the non-rotating channel piece 532 and outer sleeve 574 and/or fluid lumen 576. According to other embodiments, the proximal ports 132 and 134 are connected to separate fluid/device lumens within cannula 120. The passive gear 432 pivots on axle 518 the is held by lower housing 562 and upper housing 560. Note that the proximal portions of the upper and lower housings 560 and 562 form the male cylindrical portion 412 on single-use portion 102 (depicted in FIGS. 4A-4C). Steering wires 520 are attached their proximal ends to the passive gear 432 and at their distal ends to the bending section 320 (shown in FIGS. 3A-3C). Also shown in USB-C connector 402. The cover piece 526 forms part of the re-usable portion 104, and includes female socket 414. The distal portion of the piece 526 also includes the female opening 424 (shown in FIG. 4B). Also shown is USB-C receptacle 404. Transmission gear 434 is shown enmeshed with drive gear 510. Drive gear 510 has a square shaped central opening to accept axle piece 612 (shown in FIG. 6C). Bearings 521, outer rings 524 and bearing seals 522 are fitted as shown. The thumb lever 146, is formed to two pieces, left side 546 and right side 548, for ease of assembly. Actuating the thumb lever 146 directly rotates the drive gear 510. Also shown are springs 502 that are configured to bias the thumb lever 146 and drive gear 510 towards a central position that corresponds to the cannula 120 being in a straight position (i.e. neither bent upwards or downwards). The handle portion (140 in FIGS. 1A-1C) is formed of a top cover 542 and a bottom cover 540. Main printed circuit board (PCB) 552 is mounted to the top cover 542 using screws (not shown). Rechargeable battery 550 is mounted such that it can be accessed and replaced via battery door 148. According to some embodiments, battery 550 is an 18650-type lithium-ion battery. Electronics modules 554 mounted on PCB 552 are configured to carry out various processes such as video processing and capture, wi-fi transmission of data to external devices, lighting control, user interface processing, and diagnostics. Electronic modules 554 also are configured to include at least one non-volatile memory module for storing captured video and images from the camera module.

Note that in embodiments such as shown in FIG. 5 where the battery, printed circuit boards and various electronics modules are included within the housing of handle 140, rather than the display 150, the overall system is less "top heavy" than some other designs that have more components included in the display module. As shown in FIGS. 1A and 1B, the cannula 120, collar 170 and portion 174 are configured to rotate separately from other proximal components, including the handle 140 and display 150, as shown by arrows 124 and 122. Such embodiments have an ergonomic advantage over other embodiments in which the entire handle (as with conventional endoscope systems) or handle and integrated display module, have to be rotated along with the cannula. A further ergonomic advantage over some other designs results from the relatively close alignment of the display screen 150 and the cannula 120. As shown in FIG. 1B, the angle 190 from the distal tip 110 to the top of the display screen 150 and along the main longitudinal axis of cannula 120 is relatively small. According to some embodiments the range of angle 190 preferably is 7.5 degrees and can be in the range of 5-15 degrees. This facilitates keeping within the visual field of the user both display 150 (or at least its screen) and the distant portion of cannula 120 when the user is focused at the center of display 150. Or, when the cannula's distal end is in a patient's body, this facilitates keeping display 150 and thumb lever 146 in the user's field of vision when the user's eyes focus at the center of display 150.

Figure 6A:
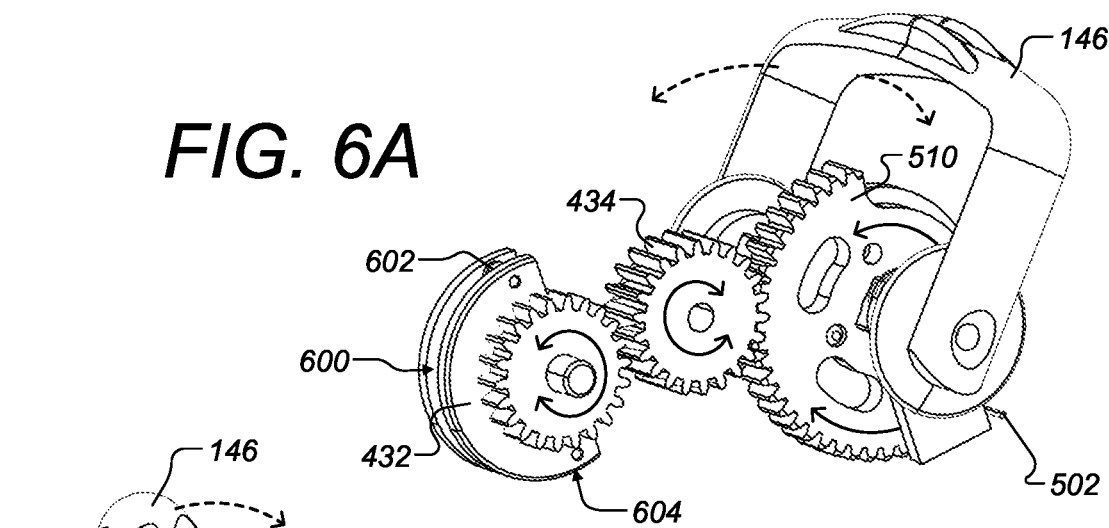
FIGS. 6A-6C are perspective views illustrating aspects of the steering structure and steering drive mechanism of a portable and ergonomic endoscope, according to some embodiments.
Figure 6B:
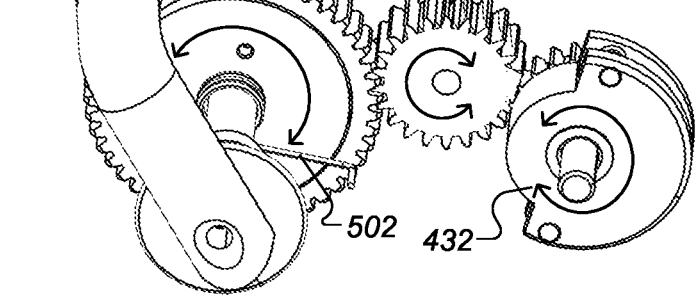
Figure 6C:
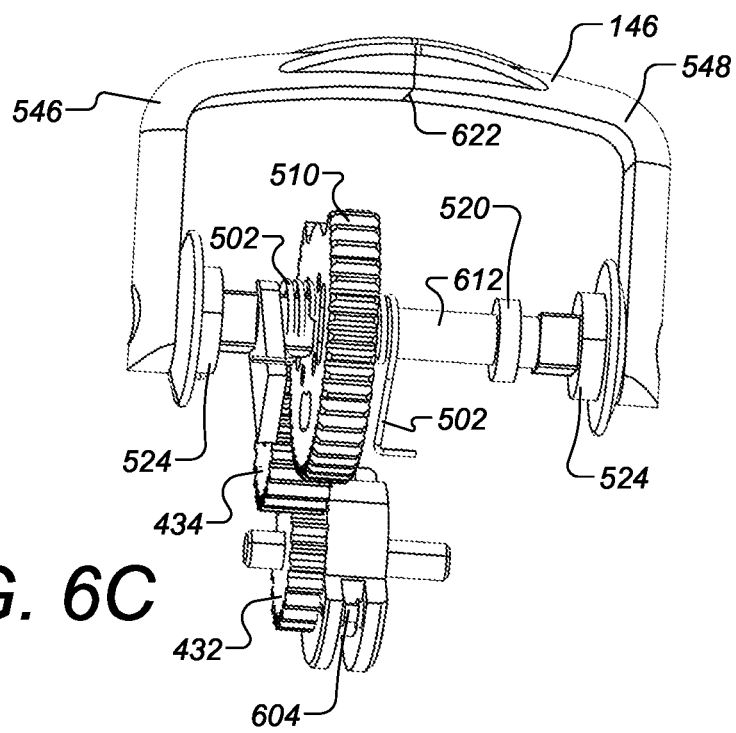

FIGS. 6A-6C are perspective views illustrating aspects of the steering structure and steering drive mechanism of a portable and ergonomic endoscope, according to some embodiments. As shown, moving the thumb lever 146 up and down as shown by the dotted arrows, causes the drive, transmission and passive gears 510, 434 and 432 to rotate as shown by the solid arrows. Passive gear 432 includes a groove 600 and upper and lower pins 602 and 604. The upper and lower steering wires (not shown) that run along the cannula to the bending section of the cannula are attached at their proximal ends to the upper and lower pins 602 and 602, respectively. Rotating the passive gear 432 causes the steering wires to tighten and loosen which causes the distal tip to bend upwards and downwards. According to some embodiments, thumb lever 146 is formed of right and left portions 546 and 548, respectively, which are joined at seam 622.

Figure 7:
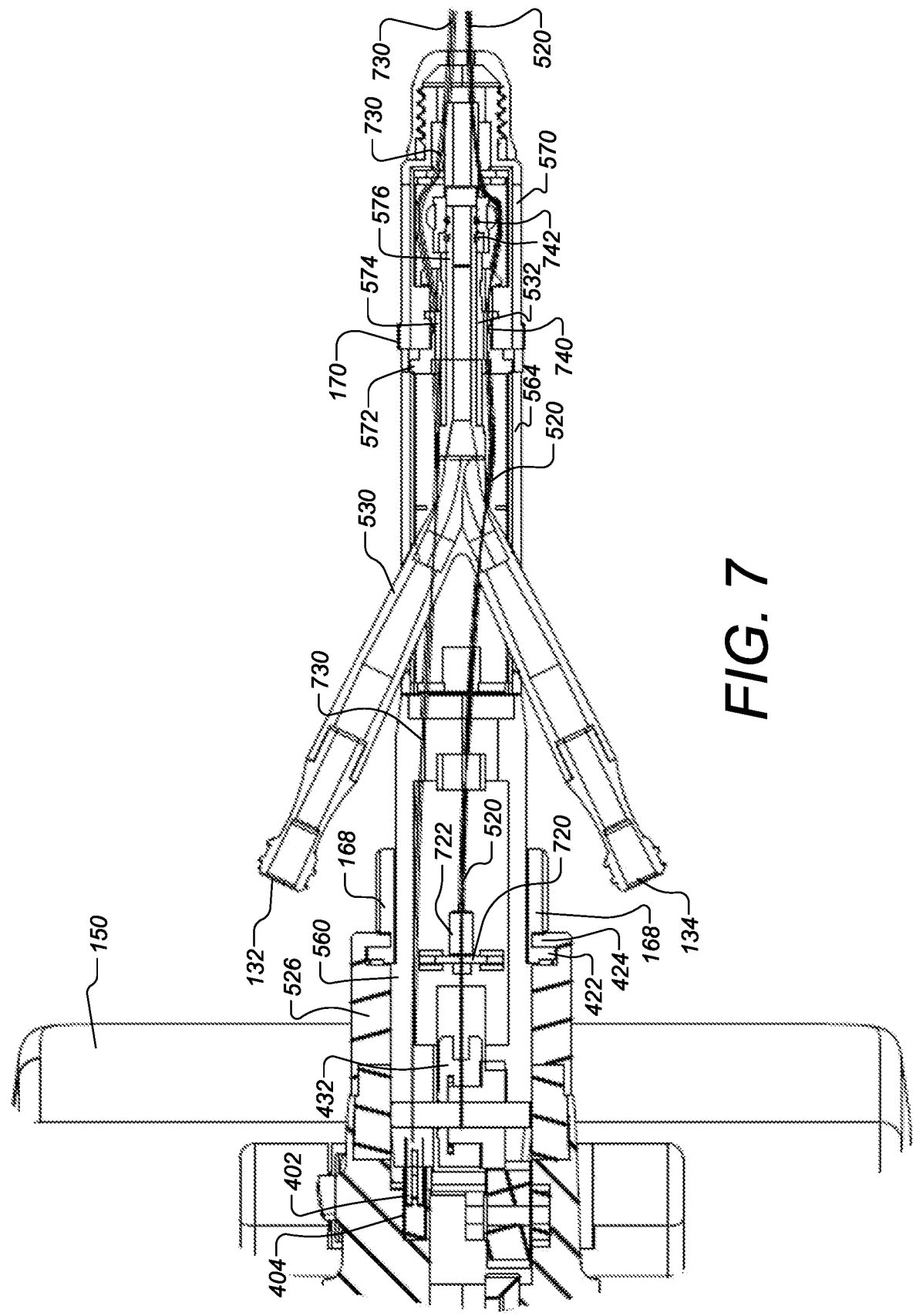
FIG. 7 is a cross-section view illustrating aspects of the fluid hub and rotatable cannula of a portable and ergonomic endoscope, according to some embodiments.

FIG. 7 is a cross-section view illustrating aspects of the fluid hub and rotatable cannula of a portable and ergonomic endoscope, according to some embodiments. FIG. 7 is a bottom view with the section being along the mid-line or main longitudinal axis of the cannula and hub. Steering wires 520 are shown, attached at their proximal ends to the passive gear 432 and at their distal ends to the bending section 320 (shown in FIGS. 3A-3C). Note that there are two steering wires 520 and with the section of FIG. 7 begin taken at the mid-line sometimes only a single wire will be visible, especially near gear 432 where their separated by a greater distance. Also shown is electrical cable 730 that runs from the distal tip and cannula (not shown in FIG. 7), and through the fluid hub as shown in FIG. 7. The electrical cable 730 is insulated and includes a plurality of electrical conductors used for powering and controlling both the LEDs and camera module (shown in FIG. 9A), as well as conveying image data from the distal tip camera module. The proximal end of cable 730 is electrically attached to USB-C type plug 402 as shown. Also shown in FIG. 7 are O-ring seals 740 and 742, which are configured to form fluid proof seals between the non-rotating channel piece 532 and rotating parts outer sleeve 574 and fluid lumen 576. Also shown in FIG. 7 are plate 720 and gromets 722. plate 720 includes two holes through which steering wires 520 pass. Also visible in FIG. 7 is the plug-and-twist type structural connection wherein a male portion 422 is shown inserted past a female opening 424.

Figure 8A:
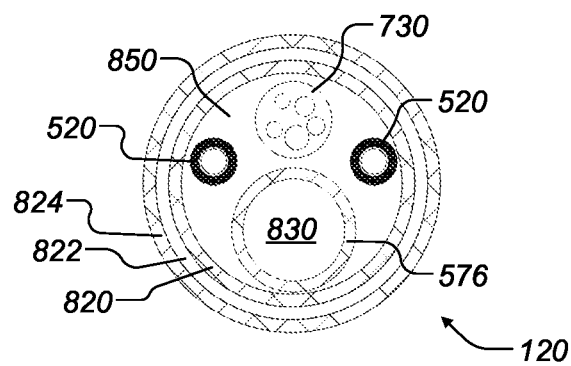
FIGS. 8A and 8B are a cross section view and side view, respectively, of a cannula of a portable and ergonomic endoscope, according to some embodiments.
Figure 8B:
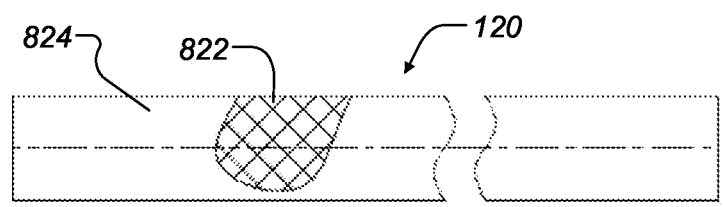

FIGS. 8A and 8B are a cross section view and side view, respectively, of a cannula of a portable and ergonomic endoscope, according to some embodiments. The outer portion of cannula 120 includes three layers: an inner metal layer 820, mesh intermediate layer 822 and polymer outer layer 824. According to some embodiments, the inner layer 820 is made of a stainless-steel material such as "SUS304". According to some embodiments intermediate layer 822 is a mesh material, such as mesh #300 and is made of a stainless-steel material such as "SUS304". According to some embodiments, the outer layer 824 is a polymer material such as Low-density polyethylene (LDPE). According to some embodiments, the thickness of layer 820 is about 0.15 mm, the thickness of layer 822 is about 0.1 mm, the thickness of layer 824 is about 0.15 mm. According to some embodiments, within the inner layer 820 of cannula 120 is electrical cable 730, steering wires 520 and fluid/device lumen wall 576, defining inner lumen 830. The electrical cable 730 is insulated and includes a plurality of electrical conductors used for powering and controlling both the LEDs and camera module (shown in FIG. 9A), as well as conveying image data from the camera module. The steering wires 520 are used to impart bending force on the bending section of the cannula. The lumen wall 576 defines fluid lumen 830. FIG. 8B shows in side view the outer layer 824 partially cut away to reveal intermediate layer 822. According to some embodiments, the lumen 830 can be used for in flow (out of the device and into the cavity or tissue), out flow (into the device from the cavity or tissue), or both in flow and out flow. Alternatively, both ports 132 and 134 can be connected to the same lumen. Furthermore, lumen 830 can be configured as a device channel for passing a device, such as needle, scraper, scalpel, etc., depending on the application. According to some embodiments, lumen 830 is configured as a device channel and has an ID of about 2.4 mm and the wall 576 has a thickness of about 0.2 mm. According to some other embodiments, the ID of lumen 830 is less than 2.4 mm and can be as small as 1.2 mm, or smaller, for some applications. According to some embodiments, the OD of cable 730 can be about 0.9 mm. According to some embodiments, the unoccupied space within inner wall layer 820 can define another "lumen" 850 that can be used to convey fluid, for example.

Figure 8C:
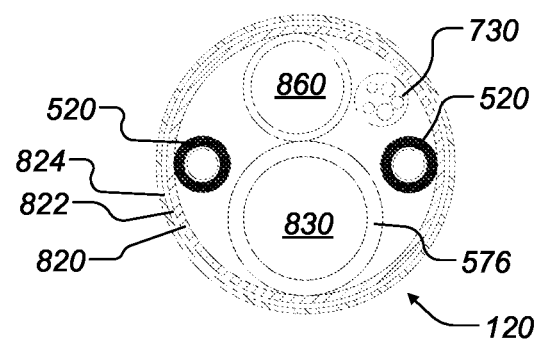
FIG. 8C is a cross section view of a multi-fluid/device lumen cannula of a portable and ergonomic endoscope, according to some embodiments.

FIG. 8C is a cross section view of a multi-fluid lumen cannula of a portable and ergonomic endoscope, according to some embodiments. According to some embodiments, within the inner layer 820 of cannula 120, in addition to electrical cable 730, steering wires 520 and fluid/device lumen 830, is another fluid lumen 860. According to some embodiments, the fluid hub (not shown in FIG. 8C) can include two proximal ports (e.g. ports 132 and 134 as shown in FIG. 1A) with one port being fluidly attached to one of fluid/device lumens 830 and 860 and the other being attached to the other fluid/device lumen.

Figure 9A:
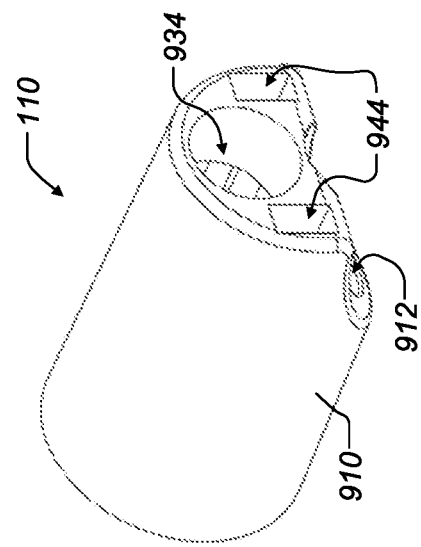
FIG. 9A partially exploded perspective view of the distal tip of a portable and ergonomic endoscope, according to some embodiments.
Figure 9A:
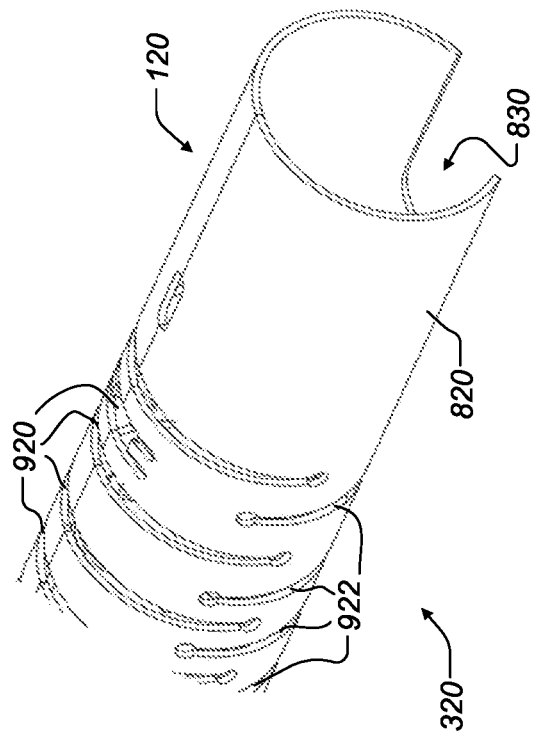

FIG. 9A partially exploded perspective view of the distal tip of a portable and ergonomic endoscope, according to some embodiments. Shown in bending section 320 of cannula 120 are a plurality of upper grooves 920 and lower grooves 922. According to some embodiments, a separate distal tip housing 910 is configured to accept the distal end of cannula 120. The housing 910 includes a circular opening 912 that is connected to fluid lumen 830 defined by lumen wall 576 (shown in FIG. 8A). The tip piece 910 also includes socket 934 for a camera module, and sockets 944 for LEDs. Lumen 850 (shown in FIG. 8A) houses electrical cable 730 (shown in FIG. 8A) and provides fluid communication to front fluid ports 950 (shown in FIG. 9C) on the distal tip 110. The distal tip 110 is shown in this example made of a separate piece 910.

FIG. 9B is a partial cross-section view of a cannula used in a portable and ergonomic endoscope, according to some embodiments. This view shows further details of the bending section 320 of the cannula 120, including the interleaved arrangement of the upper and lower grooves 920 and 922 formed in inner layer 820.

FIG. 9C is a partially exploded perspective view of the distal tip of a portable and ergonomic endoscope, according to some embodiments. Depicted is are distal tip structures that are compatible with multi-fluid lumen embodiments such as shown in FIG. 8C. Shown is an upper fluid guide 960 that is configured to connect at its proximal end to a fluid lumen such as lumen 860 (shown in FIG. 8C) and at its distal end to two front fluid ports 950 formed in tip piece 914. Also shown is the distal end of fluid lumen 830 defined by lumen wall 576 which connects fluidly to lower circular front port 912. Camera module 930, which includes lens 932 is, according to some embodiments, a CMOS-type image sensor. LEDs 940 and 942 are also shown. The camera module 930 and LEDs 940 and 942 could be configured for use in single fluid lumen embodiment such as shown FIG. 9A as well.

Figure 10A:
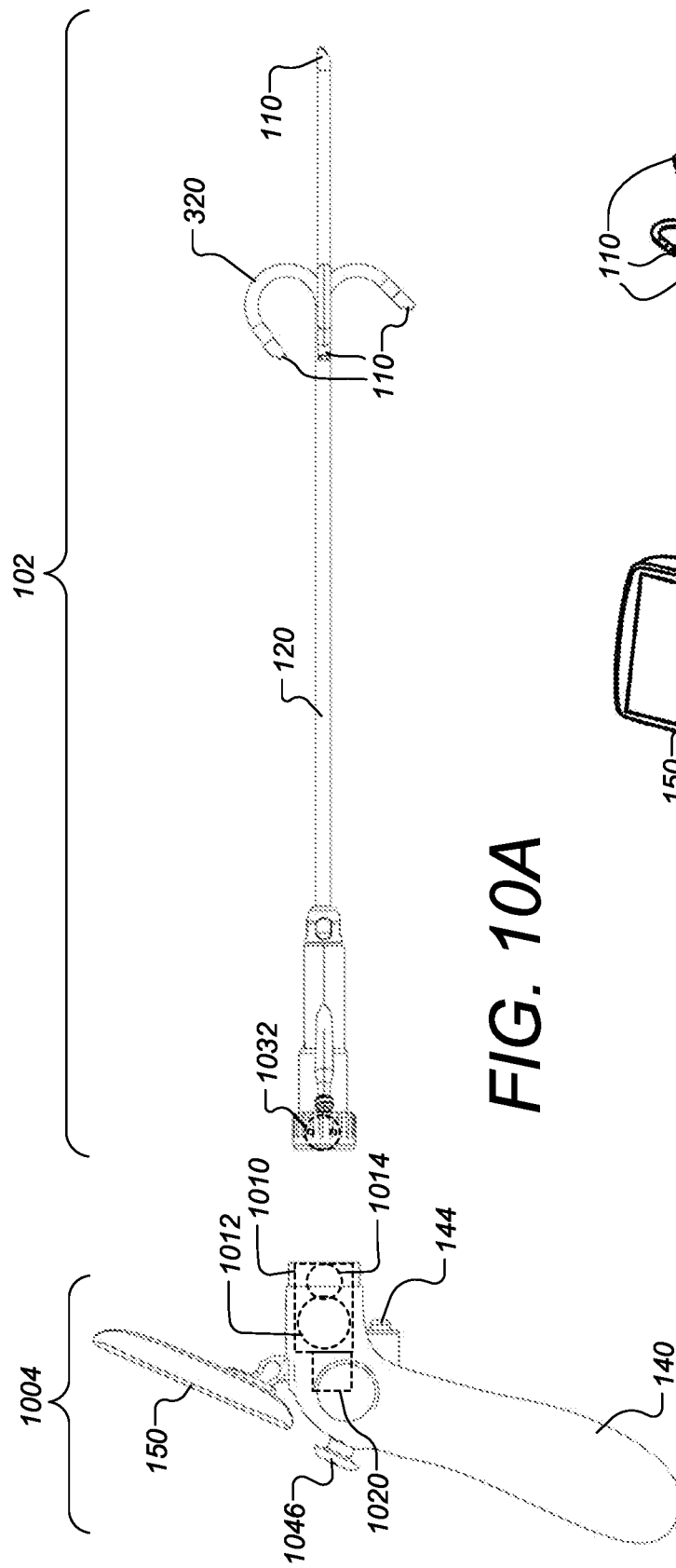
FIGS. 10A-10B are side and perspective views of a portable and ergonomic endoscope, according to some other embodiments.
Figure 10B:
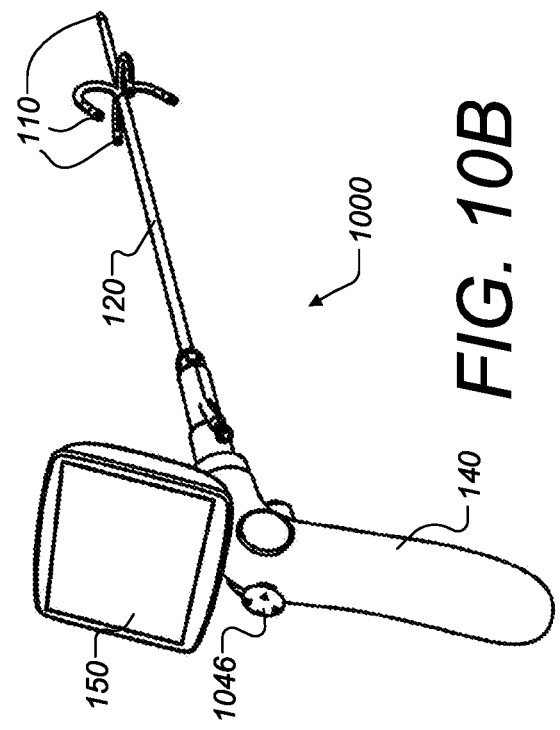

FIGS. 10A-10B are side and perspective views of a portable and ergonomic endoscope, according to some other embodiments. System 1000 is made up of a disposable, or single-use portion 102 and a re-usable portion 1004. The two portions 102 and 1004 can be mated and un-mated with each other via a "plug and twist" connector such as shown and described elsewhere herein. Apart from the steering, steering input, and steering drive mechanisms, the system 1000 is similar or identical in all aspects to the system 100 described elsewhere herein. According to some embodiments, cannula 120 is configured to steer in more than one plane. That is, in addition to upwards and downwards steering as has been shown and described elsewhere herein, the bending section 320 is configured to also provide side to side bending as shown in FIGS. 10A and 10B. According to some embodiments, this allows the distal tip to be deflected in any desired direction (i.e., to be "omni-directional"). Re-usable portion 1004, includes a joystick 1046 configured to accept user input as to desired direction and amplitude (amount) of tip deflection. A motor module 1020 is configured to provide drive forces used to cause the desired tip deflection using, for example, one or more stepper motors coupled to gearing module 1010 and controlled by the user through thumb lever 146, joystick 1046, and/or a touch screen incorporated in display 150 or on handle 140. User input controls the direction and degree of bending of portion 320 of cannula 120 and rotation of cannula 120 and/or of fluid hub 172 relative to handle piece 140 as indicated by arrows 1276 and 1274 in FIG. 12A. Motor module can be configured to stop driving bending if cannula 120 and/or rotation of cannula 120 and/or fluid hub 172 if resistance to rotation and/or bending reaches or exceeds respective thresholds, and so that further user input commanding bending of rotation does not cause motor module 1020 to exert further bending or rotation forces on cannula 120 and or fluid hub 172. Gearing module 1010 is configured to transmit the drive forces from the motor module 1020 to the mechanical interface 1032 on the single-use portion 102. According to some embodiments, a number of gears 1012 and 1014 are used to transmit the drive forces to the single-use portion 102. In cases where deflection can occur along two axes (e.g. up/down and side to side), two "transmission gears" 1014 can be used on multiple-use portion 1004, and two "passive gears" 1032 can be used on single-use portion 102. Each of the passive gears 1032 is connected to two steering wires running distally to the bending section 320 of cannula 120. A total of four steering wires provides the steering input to impart desired deflection at the bending section 320. According to some embodiments, the transmission gears 1014 and plug and twist interface on multiple-use portion 1004 are arranged so that it can be compatibly mounted to an upwards/downwards (single axis deflection) type single-use portion 102 (such as shown in FIGS. 1A-1B, 2A-2B, 3A-30, 4A-4C, etc.). In such cases, the side-to-side input from the joystick 1046 would not result in any side-to-side defection, but the upwards and downwards deflection would be fully operational. The multiple-use portion 1004, and the overall systems could be more versatile by providing the option to mate different types of single-use portions to a type single multiple-use portion, as well as different types of multiple-use portions to a single type of single use portion.

Figure 11:
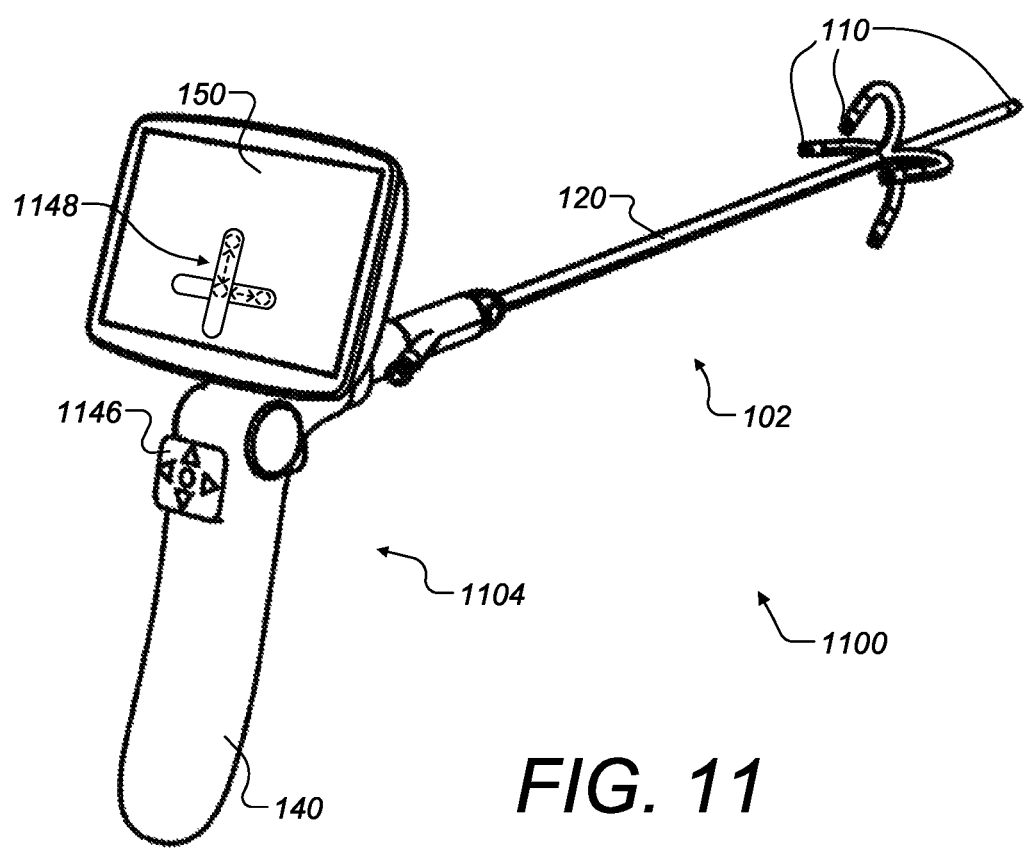
FIG. 11 is a perspective view of a portable and ergonomic endoscope, according to some other embodiments.

FIG. 11 is a perspective view of a portable and ergonomic endoscope, according to some other embodiments. System 1100 is made up of a disposable, or single-use portion 102 and a re-usable portion 1104. The two portions 102 and 1104 can be mated and un-mated with each other via a "plug and twist" connector such as shown and described elsewhere herein. Apart from the steering input, the system 1100 is similar or identical in all aspects to the system 1000 shown in FIGS. 10A-10B and described herein. For example, although not shown, it is understood that the multiple-use portion 1104 is configured with a motor module 1020 and gearing module 1010 such as shown in FIG. 10A. In the case of FIG. 11, a touch panel 1146 is used instead of the joystick 1046 of system 1000 shown in FIGS. 10A-10B. According to some embodiments, the operator can use a thumb or finger to "swipe" touch panel 1146 in different directions to control the angle and amount of deflection of the distal end of cannula 120. According to some other embodiments, display 150 is can be configured as touch-sensitive display, and an operator can touch and drag their thumb or finger on an area 1148 of the display 150 to control the angle and amount of deflection. According to some embodiments, other types of known multiple-axis user interfaces could be implemented, such as trackball, in the place of touch panel 1146.

Figure 12A:
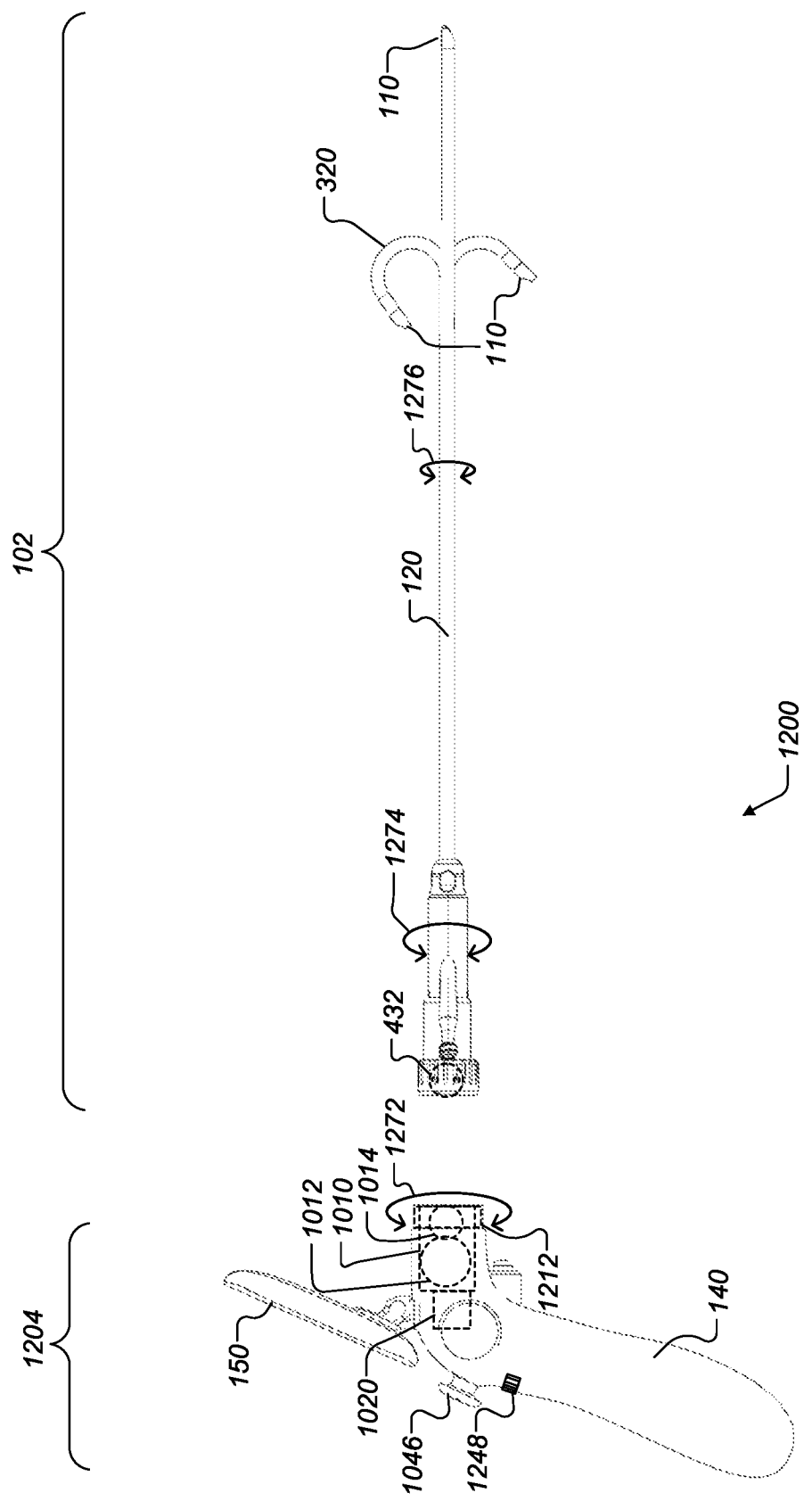
FIG. 12A is a side view of a portable and ergonomic endoscope, according to some other embodiments.

FIG. 12A is a side view of a portable and ergonomic endoscope, according to some other embodiments. System 1200 is made up of a disposable, or single-use portion 102 and a re-usable portion 1204. The two portions 102 and 1204 can be mated and un-mated with each other via a "plug and twist" connector such as shown and described elsewhere herein. Apart from the steering, steering input, and steering drive mechanisms, the system 1200 is similar or identical in all aspects to the systems 100 and 1000 described elsewhere herein. As in the embodiments shown in FIGS. 3A-3C, cannula 120 is configured to steer such that it can be deflected upwards and downwards. Re-usable portion 1204, includes a joystick 1046 configured to accept user input as to desired direction and amplitude (amount) of tip deflection. A motor module 1020 is configured to provide drive forces used to cause the desired tip deflection. Gearing module 1010 is configured to transmit the drive forces from the motor module 1020 to the mechanical interface 1032 on the single-use portion 102. According to some embodiments, gears 1012 and 1014 are used transmit the drive forces to the single-use portion 102. The passive gear 432 is connected to two steering wires running distally to the bending section 320 of cannula 120. The transmission gear 1014 and plug and twist interface on multiple-use portion 1004 are arranged so that it can be compatibly mounted to an upwards/downwards (single axis deflection) type single-use portion 102 (such as shown in FIGS. 1A-1B, 2A-2B, 3A-3C, 4A-4C, etc.). According to some embodiments, the side-to-side input from the joystick 1046 is configured to rotate the coupling piece 1212 as indicated by arrow 1272. When the single use portion 102 and multiple-use portion 1204 are mounted together, the rotation of piece 1212 causes the single-use section 102 to rotate in an identical fashion, as indicated by arrows 1274 and 1276. According to some embodiments, motor module 1020 and piece 1212 are configured to detect the precise angular position of the cannula 120 and distal tip 110. The image displayed to the user on display screen 150 is corrected to compensate for the known rotation.

Figure 12B:
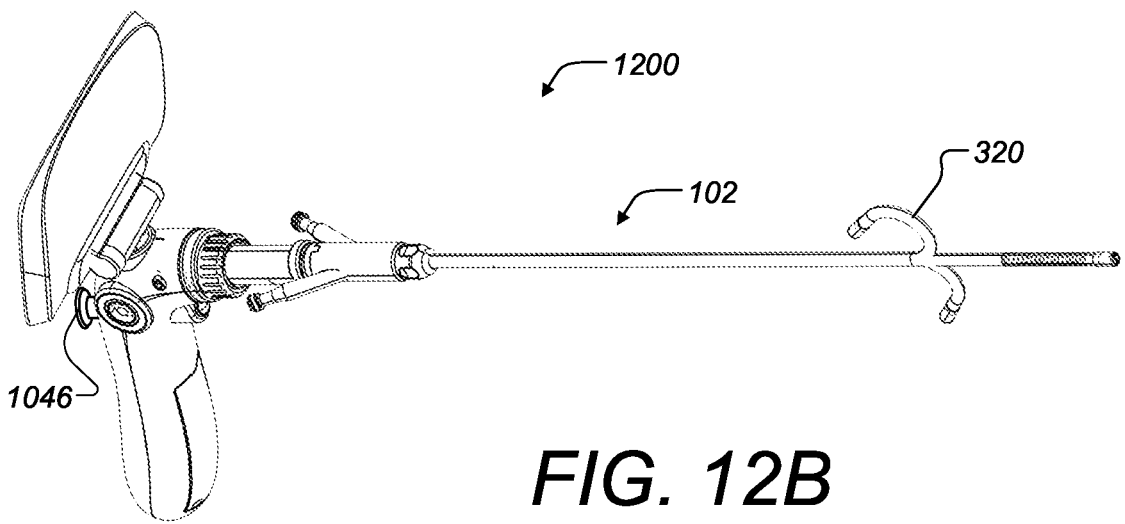
FIGS. 12B-12D are series of perspective views illustrating further aspects of the portable and ergonomic endoscope shown in FIG. 12A, according to some other embodiments.
Figure 12C:
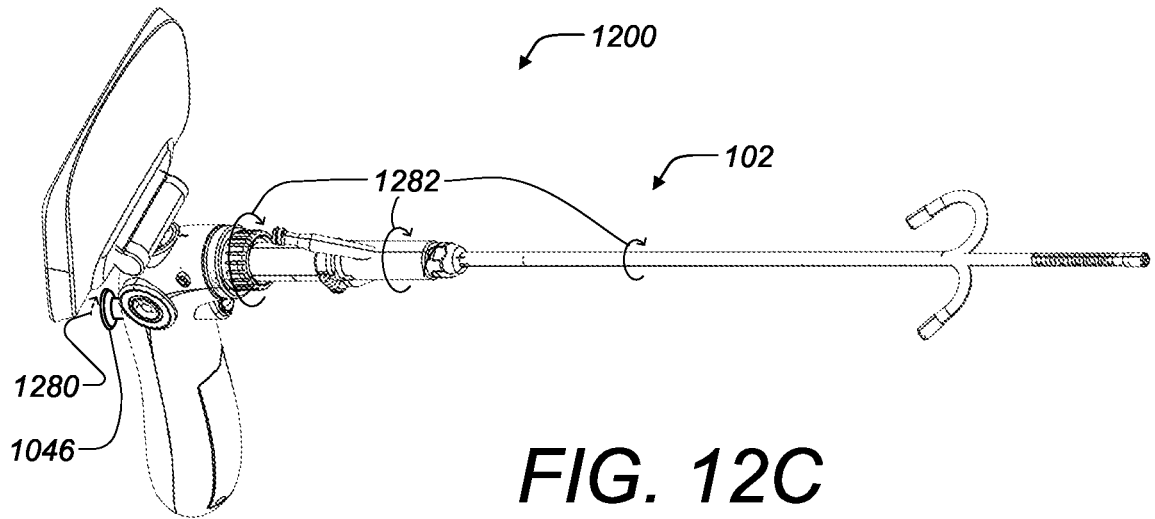
Figure 12D:
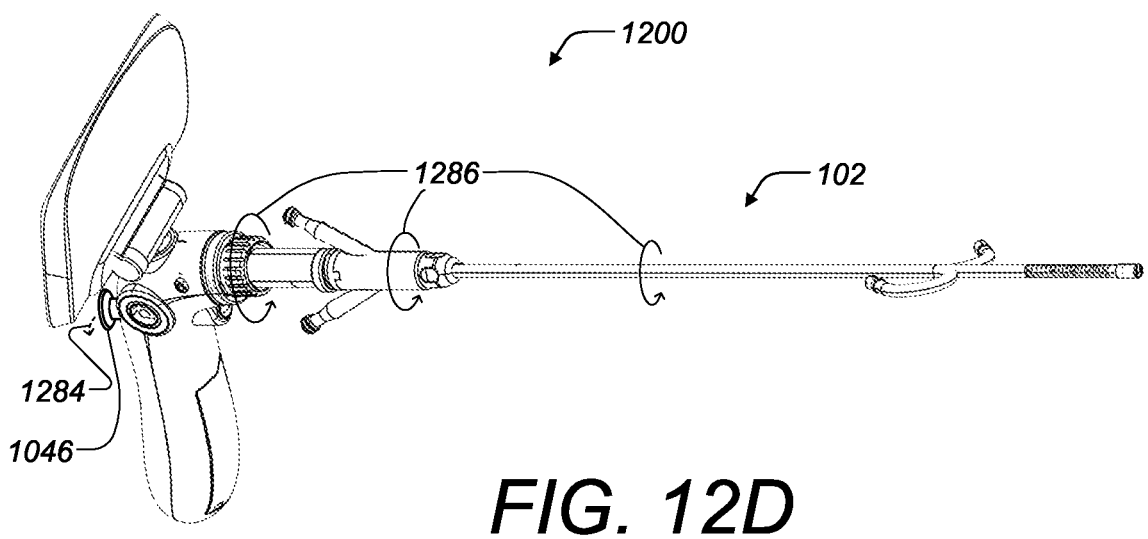

Aspects of the portable and ergonomic endoscope shown in FIG. 12A, according to some embodiments are shown in FIGS. 12B-12D. FIG. 12B shows system 1200 in the "neutral" rotation position, where the single-use portion 102 is not rotated in either direction. The bending portion 320 of the cannula will deflect upwards and downwards, depending upon the control input to joystick 1046. FIG. 12C shows single-use portion 102 rotated counter-clockwise (from the perspective of the operator) as shown by arrows 1282 in response to a left-ward movement of joystick 1046 as shown by arrow 1280. FIG. 12D shows single-use portion 102 rotated clockwise (from the perspective of the operator) as shown by arrows 1286 in response to a right-ward movement of joystick 1046 as shown by arrow 1284.

According to some embodiments, the motor module 1020 and a cannula rotation gearing module 1212 are provided that are configured to interface with single-use portion 102 to allow for motorized rotation of cannula 120 as shown by arrow 1276. According to some embodiments the proximal fluid luer ports do not rotate with cannula 120 (such is with the case with many other embodiments describe herein). According to some other embodiments, the proximal fluid luer ports do rotate with cannula 120 such as shown with arrow 1274. Such rotation will simplify some structures and reduce cost in the single-use portion 102. According to some embodiments, motorized cannula rotation allows the distal tip to be controlled omni-directionally while eliminating the need for a more complex dual-axis cannula deflection structure, especially in the more cost sensitive single-use portion of the system. According to some embodiments, types of user interfaces other than joystick can be implemented such as: touch panel; touch screen; roller ball, etc. According to some embodiments the user interface can include a separate input device, such as dial 1248 for cannula rotation.

According to some embodiments, to improve ergonomics, the joystick 1046 in the embodiments of FIGS. 10A-10B, and 12A-D can have a longer post and/or have longer "throw." Having a longer post (i.e. protruding a longer distance from the body of handle 140) or having a longer throw can facilitate fine-tuning the positioning of the distal tip.

According to some embodiments, the joystick 1046 in the embodiments of FIGS. 10A-10B, and 12A-D can be configured as either "absolute" or "relative" input devices. When configured as an absolute input device the joystick position determines the absolute position of the distal tip whereas when configured as relative input device the joystick movements control the velocity and acceleration of movement of the distal tip. In many applications where fine control over the distal tip position is needed, configuring the joystick as relative input device may be beneficial.

According to some embodiments, in the case of motorized articulation, a warning signal may be displayed to the operator when an intended movement of the distal tip is being blocked (e.g. by tissue, membrane, wall, or other physical structure). According to some embodiments, the motor module 1020 (in FIGS. 10A and 12A) is configured sense resistance beyond a threshold to the intended movement. When this occurs, a warning can be displayed on screen 150 (such as a textual message or red outline frame). Other examples of warning or indications can be haptic feedback through handle 140 or joystick 1046.

Figure 13A:
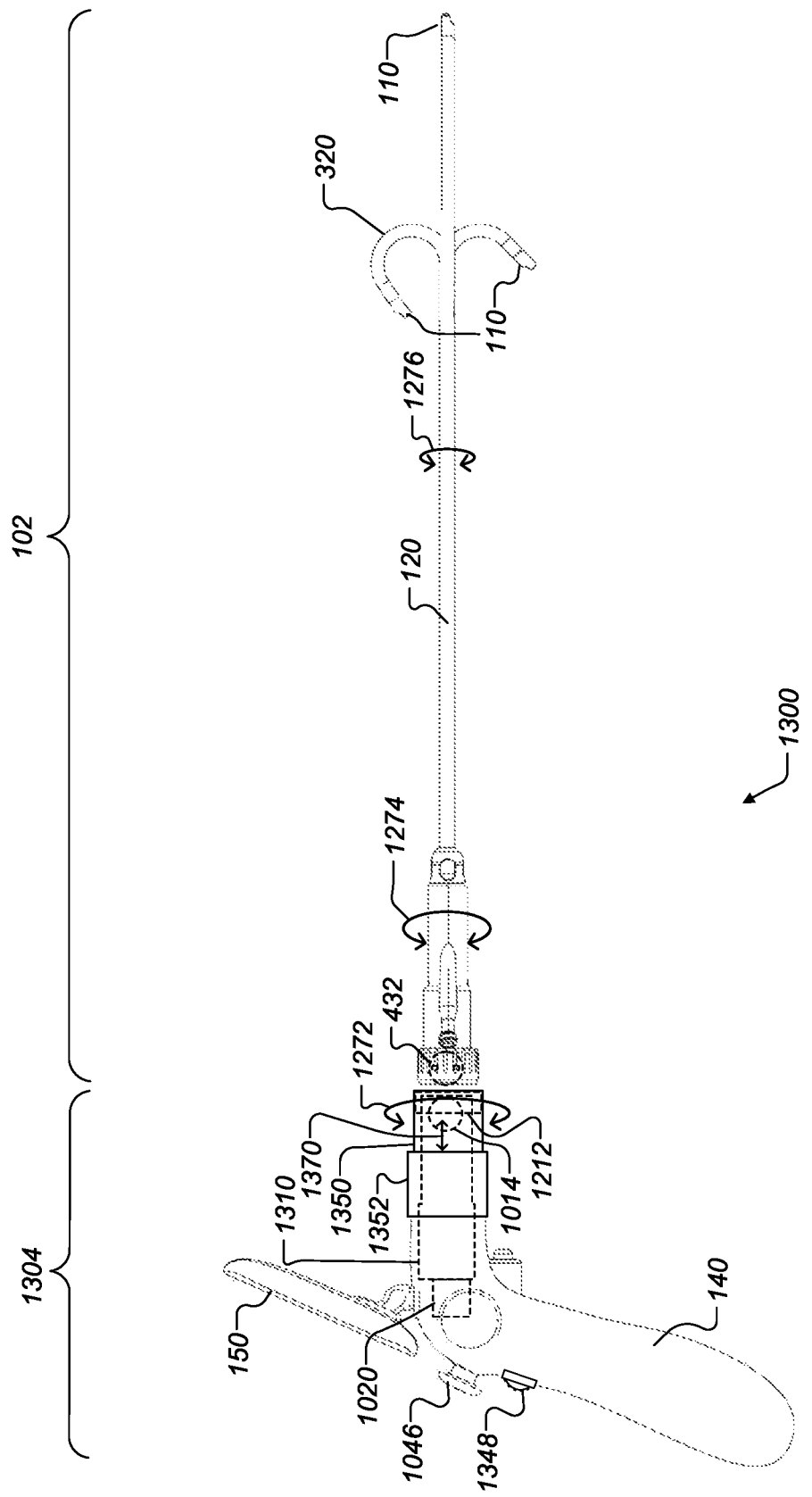
FIGS. 13A-13C illustrates in side views a portable and ergonomic endoscope, according to some other embodiments
Figure 13B:
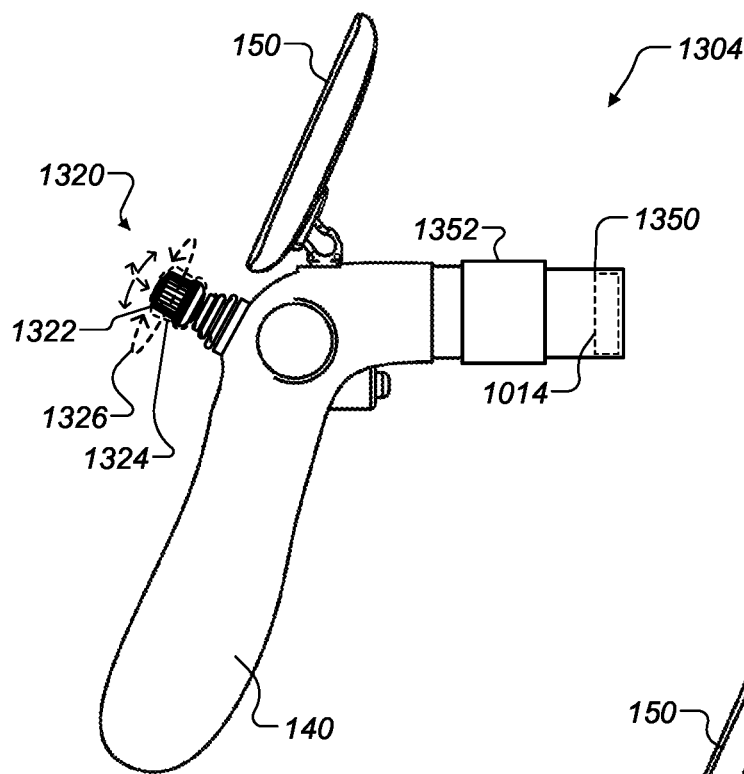
Figure 13C:
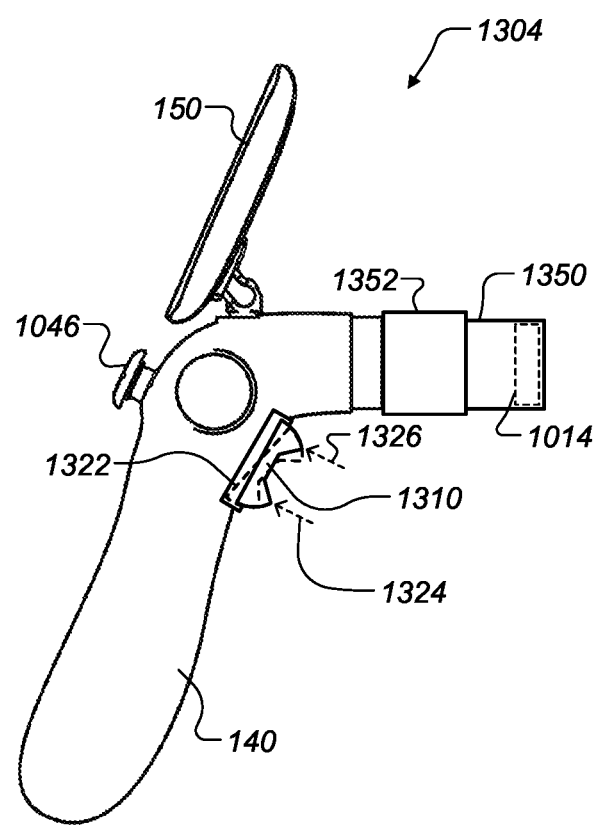

FIGS. 13A-13C illustrates in side views a portable and ergonomic endoscope, according to some other embodiments. Shown in FIG. 13A, system 1300 is made up of a disposable, or single-use portion 102 and a re-usable portion 1304. The two portions 102 and 1304 can be mated and un-mated with each other via a "plug and twist" connector such as shown and described elsewhere herein. Apart from the translational movement and control thereof, and the use of a joystick 1046 rather than thumb lever 146, the system 1300 is similar or identical in all aspects to the systems 100 and 1000 and 1200 described elsewhere herein. As in the embodiments shown in FIGS. 3A-3C, cannula 120 is configured to steer such that it can be deflected upwards and downwards. Motor module 1020 is configured to provide drive forces used to cause the desired tip deflection and translational actuation. Gearing and translation module 1310 is configured to transmit the drive forces from the motor module 1020 to passive gear 432 on the single-use portion 102. According to some embodiments, module 1310 is further configured to provide translating force parallel to the main axis of cannula 120 (when attached) as indicated by arrow 1370. According to some embodiments an inner housing 1350 is configured to slide into an outer housing 1352 to an extent that the range of translational motion can be accommodated. The transmission gear 1014 and plug and twist interface on multiple-use portion 1304 are arranged so that it can be compatibly mounted to an upwards/downwards (single axis deflection) type single-use portion 102 (such as shown in FIGS. 1A-1B, 2A-2B, 3A-3C, 4A-4C, etc.). According to some embodiments, the side-to-side input from the joystick 1046 is configured to rotate the coupling piece 1212 as indicated by arrow 1272. When the single use portion 102 and multiple-use portion 1304 are mounted together, the rotation of piece 1212 causes the single-use section 102 to rotate in an identical fashion, as indicated by arrows 1274 and 1276. Up-down motion or side-to-side motion of joystick 1046 controls deflection of the distal portion of cannula 120 as up-down motion of thumb lever controls deflection in the example of FIGS. 3A-3C. Control for the translational motion also can be from the joystick 1046. For example, joystick pushing joystick 1046 moves cannula 120 distally and, at a maximum in the distal direction the cannula automatically returns to its starting position. As an alternative, joystick 1046 can be configured such that pushing the joystick moves cannula 120 distally and the joystick can be spring-loaded so cannula 120 moves proximally when pressure on the joystick is released. As another alternative, a control input device could be provided such as dial 1348 to control the required translation while joystick 1046 is dedicated to controlling deflection of the distal portion of cannula 120.

FIG. 13B illustrates an alternative control configuration for the translational movement, according to some embodiments. In this case a 3-axis joystick 1320 is provided on handle 140. The 3-axis joystick 1320 can be tilted up and down and side to side as indicated by the solid arrows and dashed outlines 1324. This motion is like the joystick 1046 in FIGS. 12A and 10A-B, and is configured to control the steering angulation and cannula rotation as previously described herein. Additionally, joystick 3120 includes a knob 1322 that rotates as indicated by the dashed arrows 1326. Rotation of the knob 1322 is used to control the translational motion of the cannula. The operator's thumb and index finger can be used to control the tilting of the joystick as well as rotation of the knob, while the operator's other fingers and palm are used to securely support and articulate the handle 140.

FIG. 13C illustrates an alternative control for the translational movement. In this case a "seesaw" type button 1310 that includes a rocking or seesaw-type potentiometer is mounted in the "trigger" position for ergonomic use by the operator's index finger. The button 1310 can be "rocked" upwards or downwards as indicated by the dashed arrows 1326 and 1324 respectively. The downwards rocking is indicated by the dashed outline 1322.

When configured to provide translation, rotation and angulation, the multiple-use portion 1304 is similar to a robotic arm. According to some embodiments, rotation, translation and deflection can all digitally controlled and parameterized, and calibrated for particular applications. The camera at the distal tip can be uniquely and sufficiently identified by the 3D coordinates of the center of the lens and the orientation of its optical axis. These parameters can all be fed to the system for control purposes and also corrections for display when needed. The precise location of the distal tip and the direction of the camera can all be accurately determined, recorded and controlled. In this way, some embodiments described herein provide a fully robotic endoscope. Note that according to some embodiments, most of the more complex and costly aspects of the system 1300 are included in the multiple-use portion 1304, rather than in the single-use portion 102, which can significantly reduce the cost of the single-use portion and thus facilitate wider use of the endoscope system described herein.

Figure 14:
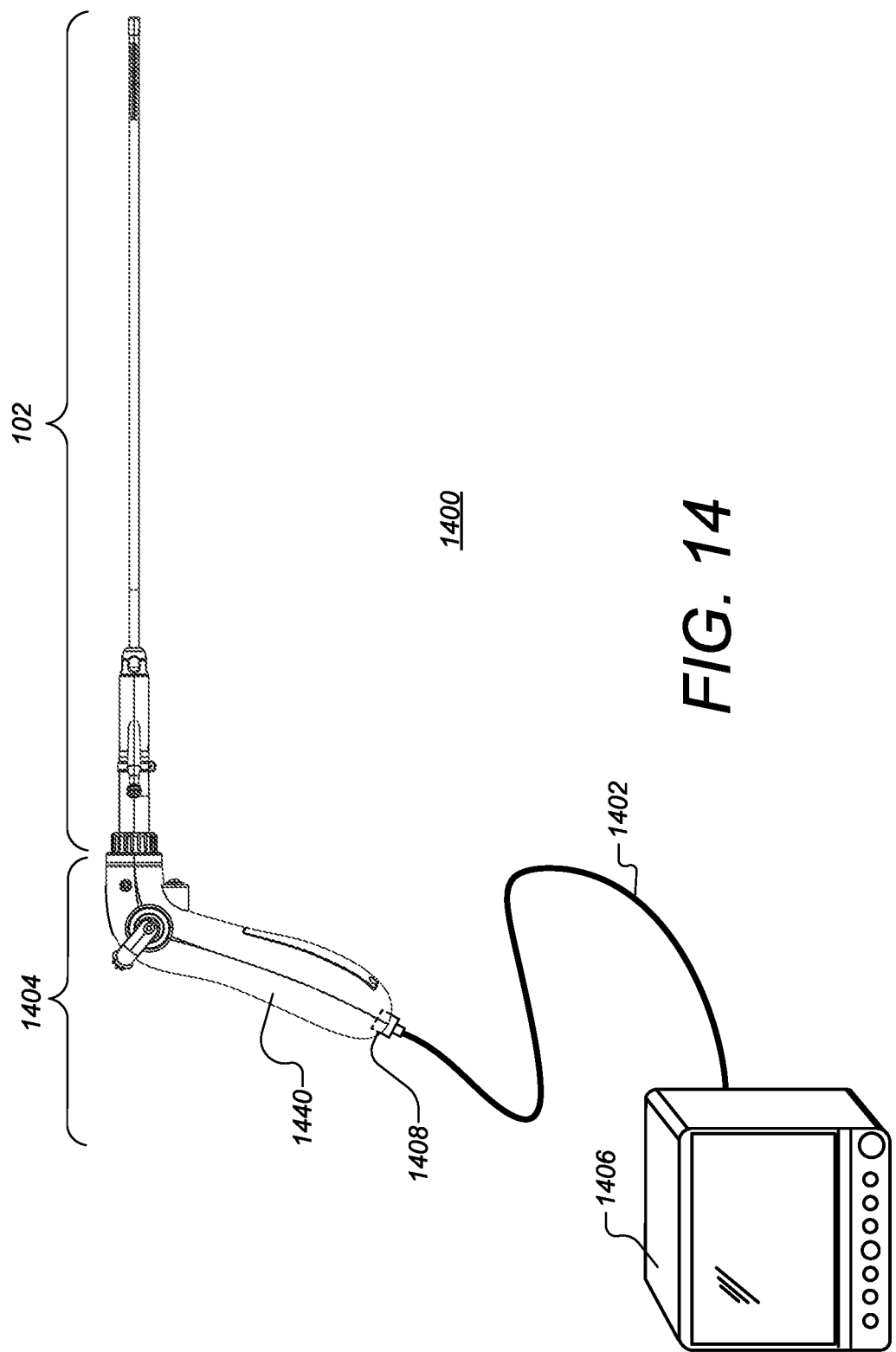
FIG. 14 illustrates in perspective an endoscope cannula and control handle configured to interact with a remote image processor and display.

FIG. 14 illustrates in perspective an endoscope cannula and control handle configured to interact with a remote image processor and display. System 1400 is made up of a single use portion 102, multiple-use control handle 1404 and processing and display unit 1406. Single-use portion 102 is similar or identical to the single use portion 102 described elsewhere herein. Multiple-use portion 1404 is like multiple-use portions 104, 1004, 1204 and 1304 described elsewhere herein, except that it includes an electrical connector 1408 that is configured for connection to processing and display unit 1406 via a cable 1402. According to some embodiments, portion 1404 may not include an integrated display screen as shown in FIG. 14. According to some other embodiments, a display screen, such as display screen 150 shown in other Figures such as FIGS. 1A AND 1B, is included in portion 1404. The two portions 102 and 1404 can be mated and un-mated with each other via a "plug and twist" connector such as shown and described elsewhere herein. Note that the processing and display unit 1406 can be located in a location (i.e. a meter or more) away from single use portion 102, multiple-use control handle 1404. One advantage of the configuration of FIG. 14 is that unit 1406 can be conveniently observed by several people and that it can be an otherwise standard workstation or hospital tower that has been programmed to interact with portions 102 and 1404.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What is claimed is:

1. An endoscope comprising:
a multiple-use portion comprising a handle and a bend-control lever extending proximally and/or upwardly therefrom, wherein:
said handle is shaped and dimensioned for a user's hand to hold said handle while ergonomically reaching and manually thumb-operating said bend-control lever; and
said handle comprises a force-generating cable driver;
a single-use portion releasably attached to said multiple-use portion and comprising:
a fluid hub extending distally from said handle and bend-control lever and having one or more proximal fluid ports;
a cannula attached to said fluid hub and extending distally therefrom along a longitudinal axis, wherein said cannula has a bendable distal portion and a distal imaging module and further has one or more distal fluid ports;
one or more lumens extending from said one or more proximal fluid ports to said one or more distal fluid ports; and
steering cables extending from the fluid hub to said bendable portion of the cannula and releasably coupled operatively to said force-generating cable driver in the multiple-use portion;
wherein said bendable portion is coupled with said bend-control lever through said force-generating cable driver such that manual operation of the bend-control lever selectively causes the bendable portion of the cannula to bend to a selected degree in a selected angular direction, including through an angle in which said imaging module has a field of view that encompasses a portion of the cannula that is promixal to said bendable portion of the cannula;
wherein the force-generating cable driver imparts to said cables the force needed to cause said bending; and
wherein said cannula is mounted for selective rotation about said longitudinal axis relative to said handle concurrently with said bending of said bendable portion of the cannula.

2. The endoscope of claim 1, in which said force-generating cable driver comprises one or more electric motors in said multiple-use portion operatively coupled with said thumb-operated bend-control lever to impart to said steering cables said force needed to cause said bending.

3. The endoscope of claim 2, in which said one or more electric motors comprise one or more stepper motors.

4. The endoscope of claim 2, in which said force-generating cable driver comprises one or more driving gears driven by said one or more electric motors.

5. The endoscope of claim 4, in which said fluid hub comprises one or more driven gears releasably mating with said one or more driving gears and operatively coupled with said steering cables to selectively bend said bendable portion of the cannula in response to rotation of the one or more driven gears.

6. The endoscope of claim 2, in which said force-generating cable driver is configured to stop applying to said steering cables the force needed to cause said bending if said bendable portion of the cannula encounters a selected threshold of resistance to bending applied to said cannula by external forces.

7. The endoscope of claim 1, in which said force-generating cable driver comprises one or more gears driven by manually imparted motion of said thumb-operated bend-control lever.

8. The endoscope of claim 1, in which said thumb-operated bend-control lever comprises a joystick.

9. The endoscope of claim 1, in which said thumb-operated bend-control lever comprise a touch-panel.

10. The endoscope of claim 1, in which said multiple-use portion further comprises a display screen mounted on said handle and operatively coupled with said imaging module to display images provided thereby, wherein said display screen includes a touch-sensitive area that selectively displays and serves as said touch-panel and responds to touch to thereby cause said force-generating cable driver to selectively bend said bendable portion of the cannula.

11. The endoscope of claim 1, in which at least one of (i) said cannula and (ii) a portion of said fluid hub that includes said proximal ports is mounted for selective rotation relative to said handle about said longitudinal axis.

12. The endoscope of claim 11, in which said cannula is mounted for rotation relative to said proximal portion of the fluid hub about said longitudinal axis.

13. The endoscope of claim 12, in which a distal portion of the fluid hub includes a collar fixedly secured to the cannula and manually rotatable to thereby rotate the cannula relative said proximal portion of the fluid hub about said longitudinal axis.

14. The endoscope of claim 11, in which said proximal portion of the fluid hub is mounted for rotation relative to the handle about said longitudinal axis.

15. The endoscope of claim 14, in which said proximal portion of the fluid hub includes a collar fixedly secured thereto and rotatable by hand to thereby rotate the proximal portion of the fluid hub relative to the handle about said longitudinal axis.

16. The endoscope of claim 11, in which said cannula is mounted for rotation relative to said proximal portion of the fluid hub and said proximal portion of the fluid hub is mounted for rotation relative to said handle.

17. The endoscope of claim 11, in which said multiple-use portion is configured to selectively cause bending of the bendable portion of the cannula concurrently with rotation of the proximal portion of the fluid hub relative to the handle.

18. An endoscope comprising:
a handle shaped and dimensioned to be grasped by a user's hand while the thumb of said hand ergonomically reaches a proximally facing control portion of the handle;
a fluid hub and a cannula extending distally therefrom along a longitudinal axis, said cannula having a distal bendable portion and a distal imaging module;
one or more driving gears in the handle and one or more driven gears in the fluid hub mating with said one or more driving gears when the fluid hub is releasably attached to the handle;
said one or more driven gears being operatively connected to said distal bendable portion of the cannula to bend said bendable distal portion of the cannula through a selected angle and in a selected angular direction upon rotation of the one or more driven gears;
wherein at least one of said cannula and said fluid hub is mounted for rotation relative to the handle when the fluid hub is releasably attached to the handle;
wherein said control portion of the handle comprises an interface responding to manual operation with the user's thumb to cause the distal bendable portion of the cannula to bend in a selected angular direction over a selected angle by imparting to said one or more driving gears the force needed to cause said bending; and
wherein said handle, fluid hub and cannula are configured for concurrent bending of said distal bendable portion of the cannula and rotation of at least one of the cannula and the fluid hub relative to the handle.

19. The endoscope of claim 18, in which said handle, fluid hub and cannula are configured for concurrent bending of said bendable portion of the cannula and rotation of each of the cannula and the fluid hub relative to the handle to thereby provide an omnidirectional view of said imaging module.

20. The endoscope of claim 18, in which said bendable portion of the cannula is configured for bending in more than one plane relative to the handle.

21. A method comprising:
releasably assembling (a) a multiple-use portion comprising a handle and a display screen mounted thereon with (b) a single use portion comprising (i) a fluid hub with one or more proximal fluid ports and (ii) a cannula extending distally from the fluid hub and having a bendable distal portion, a distal imaging module, and one or more distal ports, wherein said single-use portion further includes one or more lumens connecting said one or more proximal and distal fluid ports;
manually operating a bending control mounted on the handle of said multiple-use portion to thereby bend said bendable portion of the cannula through a selected angle in a selected angular direction;
selectively rotating at least one of the cannula and the fluid hub relative to the handle while concurrently said bendable portion of the cannula to thereby omnidirectionally point said imaging module;
displaying images from said imaging module on said display screen; and
disassembling said multiple-use portion from said single-use portion by hand, without a need for tools, and disposing of the single-use portion after a patient procedure to thereby retain the multiple-use portion for assembling with another single-use portion.

22. The method of claim 21, in which said operating the bending control comprises using the thumb of the hand holding the handle to operate a lever extending proximally from the handle.

\* \* \* \* \*